United States Patent
Endoh

(10) Patent No.: US 8,846,869 B2
(45) Date of Patent: Sep. 30, 2014

(54) MUTANT PROTEIN CAPABLE OF BINDING SPECIFICALLY AND QUICKLY TO TROPONIN I DERIVED FROM HUMAN MYOCARDIUM

(71) Applicant: Panasonic Corportion, Osaka (JP)

(72) Inventor: Takashi Endoh, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 14/152,837

(22) Filed: Jan. 10, 2014

(65) Prior Publication Data

US 2014/0206847 A1    Jul. 24, 2014

Related U.S. Application Data

(63) Continuation of application No. PCT/JP2013/001067, filed on Feb. 25, 2013.

(30) Foreign Application Priority Data

May 24, 2012 (JP) ................................ 2012-118180

(51) Int. Cl.
- *C07K 16/46* (2006.01)
- *C07K 16/18* (2006.01)
- *G01N 33/68* (2006.01)
- *G01N 33/53* (2006.01)

(52) U.S. Cl.
CPC ............. *C07K 16/18* (2013.01); *G01N 33/53* (2013.01)
USPC ................. 530/387.3; 530/380; 530/388.25; 435/7.1

(58) Field of Classification Search
None
See application file for complete search history.

(56) References Cited

U.S. PATENT DOCUMENTS

| 8,030,026 B2 | 10/2011 | Brophy et al. |
| 2006/0120960 A1 | 6/2006 | Deyev et al. |
| 2010/0216720 A1 | 8/2010 | Brophy et al. |
| 2012/0076803 A1 | 3/2012 | Brophy et al. |

FOREIGN PATENT DOCUMENTS

WO    2010/099079 A1    9/2010

OTHER PUBLICATIONS

Aleksei G. Katrukha et al., "Troponin I is released in bloodstream of patients with acute myocardial infarction not in free form but as complex," Clinical Chemistry, vol. 43, No. 8, pp. 1379-1385, (1997).
Alexander A. Kortt, et al., "Dimeric andtrinieric antibodies: high avidity scFvs for cancer targeting," Biomolecular engineering, 2001, vol. 18, No. 3, pp. 95-108.

(Continued)

*Primary Examiner* — Zachary Howard
(74) *Attorney, Agent, or Firm* — McDermott Will & Emery LLP

(57) ABSTRACT

Provided is a mutant protein capable of binding specifically and quickly to troponin I derived from human myocardium. The mutant protein comprises a first mutant scFv antibody fragment 51 a second mutant scFv antibody fragment 52 and a linker 53. The first mutant scFv antibody fragment 51 comprises a first light chain variable region 51L consisting of an amino acid sequence represented by SEQ ID NO: 76 and a first heavy chain variable region 51H consisting of an amino acid sequence represented by SEQ ID NO: 77. Similarly, the second mutant scFv antibody fragment 52 comprises amino acid sequences of SEQ ID NO: 78 and SEQ ID NO: 79. The linker 53 is provided between the C-terminus of the first heavy chain variable region 51H and the C-terminus of the second heavy chain variable region 52H.

2 Claims, 2 Drawing Sheets

(56) References Cited

OTHER PUBLICATIONS

Till Keller, M.D. et al., "Sensitive Troponin I Assay in Early Diagnosis of Acute Myocardinal Infarction," The New England Journal of Medicine, vol. 361, pp. 868-877 (2009).

Jun Kamishikiryo et al, "Molecular Basis for LLTI Protein Recognition by Human CD161 Protein (NKRPIA/KLRB1)," The Journal of Biological Chemistry, vol. 286, No. 27, pp. 23823-23830.

G. Köhler et al., "Pillars Article: Continuous cultures of fused cells secreting antibody of predefined specificity," Nature, vol. 256, (5517): pp. 495-497 (1975).

International Search Report issued in International Application No. PCT/JP2013/001067, with Date of mailing May 21, 2013.

SEQUENCE LISTING

<160> NUMBER OF SEQ ID NOS: 81

<210> SEQ ID NO 1
<211> LENGTH: 47
<212> TYPE: PRT
<213> ORGANISM: Artificial
<220> FEATURE:
<223> OTHER INFORMATION: Epitope of troponin I derived from human myocardium

<400> SEQUENCE: 1

Cys Arg Pro Ala Pro Ala Pro Ile Arg Arg Ser Ser Asn Tyr Arg
1               5                   10                  15

Ala Tyr Ala Thr Glu Pro His Ala Lys Lys Ser Lys Ile Ser Ala
                20                  25                  30

Ser Arg Lys Leu Gln Leu Lys Thr Leu Leu Leu Gln Ile Ala Lys
            35                  40                  45

<210> SEQ ID NO 2
<211> LENGTH: 50
<212> TYPE: DNA
<213> ORGANISM: Artificial
<220> FEATURE:
<223> OTHER INFORMATION: primer

<400> SEQUENCE: 2
cctttctatg cggcccagcc ggccatggcc gayattgtwc tcwcccartc         50

<210> SEQ ID NO 3
<211> LENGTH: 50
<212> TYPE: DNA
<213> ORGANISM: Artificial
<220> FEATURE:
<223> OTHER INFORMATION: primer

<400> SEQUENCE: 3
cctttctatg cggcccagcc ggccatggcc gayattstgm tsacycagtc         50

<210> SEQ ID NO 4
<211> LENGTH: 50
<212> TYPE: DNA
<213> ORGANISM: Artificial
<220> FEATURE:
<223> OTHER INFORMATION: primer

<400> SEQUENCE: 4
cctttctatg cggcccagcc ggccatggcc gayattgtgm tmactcagtc         50

<210> SEQ ID NO 5
<211> LENGTH: 50
<212> TYPE: DNA
<213> ORGANISM: Artificial
<220> FEATURE:
<223> OTHER INFORMATION: primer

<400> SEQUENCE: 5
cctttctatg cggcccagcc ggccatggcc gayattgtgh trwcacagtc         50

<210> SEQ ID NO 6
<211> LENGTH: 50
<212> TYPE: DNA
<213> ORGANISM: Artificial
<220> FEATURE:
<223> OTHER INFORMATION: primer

<400> SEQUENCE: 6
cctttctatg cggcccagcc ggccatggcc gayattgtra tgacmcagtc         50

<210> SEQ ID NO 7
<211> LENGTH: 50
<212> TYPE: DNA
<213> ORGANISM: Artificial
<220> FEATURE:
<223> OTHER INFORMATION: primer

<400> SEQUENCE: 7
cctttctatg cggcccagcc ggccatggcc gayattmaga tramccagtc            50

<210> SEQ ID NO 8
<211> LENGTH: 50
<212> TYPE: DNA
<213> ORGANISM: Artificial
<220> FEATURE:
<223> OTHER INFORMATION: primer

<400> SEQUENCE: 8
cctttctatg cggcccagcc ggccatggcc gayattcaga tgaydcagtc            50

<210> SEQ ID NO 9
<211> LENGTH: 50
<212> TYPE: DNA
<213> ORGANISM: Artificial
<220> FEATURE:
<223> OTHER INFORMATION: primer

<400> SEQUENCE: 9
cctttctatg cggcccagcc ggccatggcc gayattttgc tgactcagtc            50

<210> SEQ ID NO 10
<211> LENGTH: 50
<212> TYPE: DNA
<213> ORGANISM: Artificial
<220> FEATURE:
<223> OTHER INFORMATION: primer

<400> SEQUENCE: 10
cctttctatg cggcccagcc ggccatggcc gayattgttc tcawccagtc            50

<210> SEQ ID NO 11
<211> LENGTH: 50
<212> TYPE: DNA
<213> ORGANISM: Artificial
<220> FEATURE:
<223> OTHER INFORMATION: primer

<400> SEQUENCE: 11
cctttctatg cggcccagcc ggccatggcc gayattgwgc tsacccaatc            50

<210> SEQ ID NO 12
<211> LENGTH: 50
<212> TYPE: DNA
<213> ORGANISM: Artificial
<220> FEATURE:
<223> OTHER INFORMATION: primer

<400> SEQUENCE: 12
cctttctatg cggcccagcc ggccatggcc gayattstra tgacccartc            50

<210> SEQ ID NO 13
<211> LENGTH: 50
<212> TYPE: DNA
<213> ORGANISM: Artificial
<220> FEATURE:
<223> OTHER INFORMATION: primer

<400> SEQUENCE: 13
cctttctatg cggcccagcc ggccatggcc gayrttktga tgacccavac            50

<210> SEQ ID NO 14
<211> LENGTH: 50

```
<212> TYPE: DNA
<213> ORGANISM: Artificial
<220> FEATURE:
<223> OTHER INFORMATION: primer

<400> SEQUENCE: 14
cctttctatg cggcccagcc ggccatggcc gayatycaga tgacacagac        50

<210> SEQ ID NO 15
<211> LENGTH: 50
<212> TYPE: DNA
<213> ORGANISM: Artificial
<220> FEATURE:
<223> OTHER INFORMATION: primer

<400> SEQUENCE: 15
cctttctatg cggcccagcc ggccatggcc gayattgtga tgacacaacc        50

<210> SEQ ID NO 16
<211> LENGTH: 50
<212> TYPE: DNA
<213> ORGANISM: Artificial
<220> FEATURE:
<223> OTHER INFORMATION: primer

<400> SEQUENCE: 16
cctttctatg cggcccagcc ggccatggcc gayatccagc tgactcagcc        50

<210> SEQ ID NO 17
<211> LENGTH: 50
<212> TYPE: DNA
<213> ORGANISM: Artificial
<220> FEATURE:
<223> OTHER INFORMATION: primer

<400> SEQUENCE: 17
cctttctatg cggcccagcc ggccatggcc gayattgtga tgacbcagkc        50

<210> SEQ ID NO 18
<211> LENGTH: 50
<212> TYPE: DNA
<213> ORGANISM: Artificial
<220> FEATURE:
<223> OTHER INFORMATION: primer

<400> SEQUENCE: 18
cctttctatg cggcccagcc ggccatggcc gayattgtga taacycagga        50

<210> SEQ ID NO 19
<211> LENGTH: 50
<212> TYPE: DNA
<213> ORGANISM: Artificial
<220> FEATURE:
<223> OTHER INFORMATION: primer

<400> SEQUENCE: 19
cctttctatg cggcccagcc ggccatggcc gayattgtga tgacccagwt        50

<210> SEQ ID NO 20
<211> LENGTH: 50
<212> TYPE: DNA
<213> ORGANISM: Artificial
<220> FEATURE:
<223> OTHER INFORMATION: primer

<400> SEQUENCE: 20
```

```
cctttctatg cggcccagcc ggccatggcc gaygtgstgm tsacycagtc              50
```

<210> SEQ ID NO 21
<211> LENGTH: 52
<212> TYPE: DNA
<213> ORGANISM: Artificial
<220> FEATURE:
<223> OTHER INFORMATION: primer

<400> SEQUENCE: 21

```
cctttctatg cggcccagcc ggccatggcc gaygctgttg tactcaggaa tc           52
```

<210> SEQ ID NO 22
<211> LENGTH: 50
<212> TYPE: DNA
<213> ORGANISM: Artificial
<220> FEATURE:
<223> OTHER INFORMATION: primer

<400> SEQUENCE: 22

```
cctttctatg cggcccagcc ggccatggcc gayattgtdh tvwchcagtc              50
```

<210> SEQ ID NO 23
<211> LENGTH: 53
<212> TYPE: DNA
<213> ORGANISM: Artificial
<220> FEATURE:
<223> OTHER INFORMATION: primer

<400> SEQUENCE: 23

```
agcggcggcg gcggctctgg tggtggtgga tccgakgtrm agcttcagga gyc          53
```

<210> SEQ ID NO 24
<211> LENGTH: 53
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (39)..(39)
<223> OTHER INFORMATION: n stands for any base

<400> SEQUENCE: 24

```
agcggcggcg gcggctctgg tggtggtgga tccgaggtnc agctbcagca gtc          53
```

<210> SEQ ID NO 25
<211> LENGTH: 53
<212> TYPE: DNA
<213> ORGANISM: Artificial
<220> FEATURE:
<223> OTHER INFORMATION: primer

<400> SEQUENCE: 25

```
agcggcggcg gcggctctgg tggtggtgga tcccaggtgc agctgaagsa stc          53
```

<210> SEQ ID NO 26
<211> LENGTH: 53
<212> TYPE: DNA
<213> ORGANISM: Artificial
<220> FEATURE:
<223> OTHER INFORMATION: primer

<400> SEQUENCE: 26

```
agcggcggcg gcggctctgg tggtggtgga tcccagstbc agctgcagca gtc          53
```

<210> SEQ ID NO 27
<211> LENGTH: 53
<212> TYPE: DNA
<213> ORGANISM: Artificial
<220> FEATURE:
<223> OTHER INFORMATION: primer

<400> SEQUENCE: 27
agcggcggcg gcggctctgg tggtggtgga tccgaggtyc agctycagca gtc                53

<210> SEQ ID NO 28
<211> LENGTH: 53
<212> TYPE: DNA
<213> ORGANISM: Artificial
<220> FEATURE:
<223> OTHER INFORMATION: primer

<400> SEQUENCE: 28
agcggcggcg gcggctctgg tggtggtgga tccgargtcc arctgcaaca rtc                53

<210> SEQ ID NO 29
<211> LENGTH: 53
<212> TYPE: DNA
<213> ORGANISM: Artificial
<220> FEATURE:
<223> OTHER INFORMATION: primer

<400> SEQUENCE: 29
agcggcggcg gcggctctgg tggtggtgga tcccaggtyc agctbcagca rtc                53

<210> SEQ ID NO 30
<211> LENGTH: 53
<212> TYPE: DNA
<213> ORGANISM: Artificial
<220> FEATURE:
<223> OTHER INFORMATION: primer

<400> SEQUENCE: 30
agcggcggcg gcggctctgg tggtggtgga tcccaggtyc arctkcagca gtc                53

<210> SEQ ID NO 31
<211> LENGTH: 53
<212> TYPE: DNA
<213> ORGANISM: Artificial
<220> FEATURE:
<223> OTHER INFORMATION: primer

<400> SEQUENCE: 31
agcggcggcg gcggctctgg tggtggtgga tcccaggtcc acgtgaagca gtc                53

<210> SEQ ID NO 32
<211> LENGTH: 53
<212> TYPE: DNA
<213> ORGANISM: Artificial
<220> FEATURE:
<223> OTHER INFORMATION: primer

<400> SEQUENCE: 32
agcggcggcg gcggctctgg tggtggtgga tccgaggtga asstggtgga rtc                53

<210> SEQ ID NO 33
<211> LENGTH: 53
<212> TYPE: DNA
<213> ORGANISM: Artificial
<220> FEATURE:
<223> OTHER INFORMATION: primer

```
<400> SEQUENCE: 33
agcggcggcg gcggctctgg tggtggtgga tccgavgtga wgytggtgga gtc        53

<210> SEQ ID NO 34
<211> LENGTH: 53
<212> TYPE: DNA
<213> ORGANISM: Artificial
<220> FEATURE:
<223> OTHER INFORMATION: primer

<400> SEQUENCE: 34
agcggcggcg gcggctctgg tggtggtgga tccgaggtga aggtcatcga gtc        53

<210> SEQ ID NO 35
<211> LENGTH: 53
<212> TYPE: DNA
<213> ORGANISM: Artificial
<220> FEATURE:
<223> OTHER INFORMATION: primer

<400> SEQUENCE: 35
agcggcggcg gcggctctgg tggtggtgga tccsaggtgc agskggtgga gtc        53

<210> SEQ ID NO 36
<211> LENGTH: 53
<212> TYPE: DNA
<213> ORGANISM: Artificial
<220> FEATURE:
<223> OTHER INFORMATION: primer

<400> SEQUENCE: 36
agcggcggcg gcggctctgg tggtggtgga tccgakgtgc amctggtgga gtc        53

<210> SEQ ID NO 37
<211> LENGTH: 53
<212> TYPE: DNA
<213> ORGANISM: Artificial
<220> FEATURE:
<223> OTHER INFORMATION: primer

<400> SEQUENCE: 37
agcggcggcg gcggctctgg tggtggtgga tccgaagtgc avctggtgga gtc        53

<210> SEQ ID NO 38
<211> LENGTH: 53
<212> TYPE: DNA
<213> ORGANISM: Artificial
<220> FEATURE:
<223> OTHER INFORMATION: primer

<400> SEQUENCE: 38
agcggcggcg gcggctctgg tggtggtgga tccgaggtga agctgatgga rtc        53

<210> SEQ ID NO 39
<211> LENGTH: 53
<212> TYPE: DNA
<213> ORGANISM: Artificial
<220> FEATURE:
<223> OTHER INFORMATION: primer

<400> SEQUENCE: 39
agcggcggcg gcggctctgg tggtggtgga tccgaggtgc arcttgttga gtc        53

<210> SEQ ID NO 40
<211> LENGTH: 53
```

<210> SEQ ID NO 40
<211> LENGTH: 53
<212> TYPE: DNA
<213> ORGANISM: Artificial
<220> FEATURE:
<223> OTHER INFORMATION: primer

<400> SEQUENCE: 40
agcggcggcg gcggctctgg tggtggtgga tccgargtra agcttctcga gtc      53

<210> SEQ ID NO 41
<211> LENGTH: 53
<212> TYPE: DNA
<213> ORGANISM: Artificial
<220> FEATURE:
<223> OTHER INFORMATION: primer

<400> SEQUENCE: 41
agcggcggcg gcggctctgg tggtggtgga tccgaagtga arsttgagga gtc      53

<210> SEQ ID NO 42
<211> LENGTH: 53
<212> TYPE: DNA
<213> ORGANISM: Artificial
<220> FEATURE:
<223> OTHER INFORMATION: primer

<400> SEQUENCE: 42
agcggcggcg gcggctctgg tggtggtgga tccgaagtga tgctggtgga gtc      53

<210> SEQ ID NO 43
<211> LENGTH: 55
<212> TYPE: DNA
<213> ORGANISM: Artificial
<220> FEATURE:
<223> OTHER INFORMATION: primer

<400> SEQUENCE: 43
agcggcggcg gcggctctgg tggtggtgga tcccaggtta ctctraaagw gtstg    55

<210> SEQ ID NO 44
<211> LENGTH: 53
<212> TYPE: DNA
<213> ORGANISM: Artificial
<220> FEATURE:
<223> OTHER INFORMATION: primer

<400> SEQUENCE: 44
agcggcggcg gcggctctgg tggtggtgga tcccaggtcc aaytvcagca rcc      53

<210> SEQ ID NO 45
<211> LENGTH: 53
<212> TYPE: DNA
<213> ORGANISM: Artificial
<220> FEATURE:
<223> OTHER INFORMATION: primer

<400> SEQUENCE: 45
agcggcggcg gcggctctgg tggtggtgga tccgatgtga acttggaagt gtc      53

<210> SEQ ID NO 46
<211> LENGTH: 53
<212> TYPE: DNA
<213> ORGANISM: Artificial
<220> FEATURE:
<223> OTHER INFORMATION: primer

<400> SEQUENCE: 46

```
accagagccg ccgccgccgc taccaccacc accccgtttg atttccarct tkg          53
```

<210> SEQ ID NO 47
<211> LENGTH: 53
<212> TYPE: DNA
<213> ORGANISM: Artificial
<220> FEATURE:
<223> OTHER INFORMATION: primer

<400> SEQUENCE: 47

```
accagagccg ccgccgccgc taccaccacc accccgtttt atttccagct tgg          53
```

<210> SEQ ID NO 48
<211> LENGTH: 53
<212> TYPE: DNA
<213> ORGANISM: Artificial
<220> FEATURE:
<223> OTHER INFORMATION: primer

<400> SEQUENCE: 48

```
accagagccg ccgccgccgc taccaccacc accccgttts agctccagct tgg          53
```

<210> SEQ ID NO 49
<211> LENGTH: 53
<212> TYPE: DNA
<213> ORGANISM: Artificial
<220> FEATURE:
<223> OTHER INFORMATION: primer

<400> SEQUENCE: 49

```
accagagccg ccgccgccgc taccaccacc accccgttyw atttccaact twg          53
```

<210> SEQ ID NO 50
<211> LENGTH: 53
<212> TYPE: DNA
<213> ORGANISM: Artificial
<220> FEATURE:
<223> OTHER INFORMATION: primer

<400> SEQUENCE: 50

```
accagagccg ccgccgccgc taccaccacc accccctagg acagtcagtt tgg          53
```

<210> SEQ ID NO 51
<211> LENGTH: 45
<212> TYPE: DNA
<213> ORGANISM: Artificial
<220> FEATURE:
<223> OTHER INFORMATION: primer

<400> SEQUENCE: 51

```
cggcaccggc gcacctgcgg ccgcygagga aacggtgacc gtggt                   45
```

<210> SEQ ID NO 52
<211> LENGTH: 45
<212> TYPE: DNA
<213> ORGANISM: Artificial
<220> FEATURE:
<223> OTHER INFORMATION: primer

<400> SEQUENCE: 52

```
cggcaccggc gcacctgcgg ccgcygagga gactgtgaga gtggt                   45
```

<210> SEQ ID NO 53
<211> LENGTH: 45
<212> TYPE: DNA
<213> ORGANISM: Artificial

<220> FEATURE:
<223> OTHER INFORMATION: primer

<400> SEQUENCE: 53
cggcaccggc gcacctgcgg ccgcygagga dacggtgact gagrt            45

<210> SEQ ID NO 54
<211> LENGTH: 45
<212> TYPE: DNA
<213> ORGANISM: Artificial
<220> FEATURE:
<223> OTHER INFORMATION: primer

<400> SEQUENCE: 54
cggcaccggc gcacctgcgg ccgcygagga agactgtaga gtggt            45

<210> SEQ ID NO 55
<211> LENGTH: 45
<212> TYPE: DNA
<213> ORGANISM: Artificial
<220> FEATURE:
<223> OTHER INFORMATION: primer

<400> SEQUENCE: 55
cggcaccggc gcacctgcgg ccgcygcgga gacastgacc agagt            45

<210> SEQ ID NO 56
<211> LENGTH: 45
<212> TYPE: DNA
<213> ORGANISM: Artificial
<220> FEATURE:
<223> OTHER INFORMATION: primer

<400> SEQUENCE: 56
cggcaccggc gcacctgcgg ccgcygcaga gacastgacc agagt            45

<210> SEQ ID NO 57
<211> LENGTH: 345
<212> TYPE: DNA
<213> ORGANISM: Artificial
<220> FEATURE:
<223> OTHER INFORMATION: base sequence coding for VH chain of monoclonal
      antibody

<400> SEQUENCE: 57
cagctgcagc tgcagcagtc tggggcagag cttgtgaggt caggggcctc agtcaagttg    60
tcctgcacag cttctggctt caacattaaa gactactata tgaactgggt gaagcagagg   120
cctgaacagg gcctggagtg gattggatgg attgatcctg cgaatggtga tactgcatat   180
gccccgaggt tccaggtcaa ggccactatg actgcagaca atcctccaa cacagcctac    240 ctgcagctca gcagcctgac atctgaggac actgccgtct attactgtaa tgctgatctc   300
cctatggacc agtggggtca aggaacctca gtcaccgtct cctca                   345

<210> SEQ ID NO 58
<211> LENGTH: 339
<212> TYPE: DNA
<213> ORGANISM: Artificial
<220> FEATURE:
<223> OTHER INFORMATION: base sequence coding for VL chain of monoclonal
      antibody

<400> SEQUENCE: 58
gacgtggtgc tcactcagtc tccactcact ttgtcggtta ccattggaca accagcctcc    60
atctcttgca agtcaagtca gagcctctta gatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
ctcacgttcg gtgctgggac aaagttggaa attaaacgg                           339

<210> SEQ ID NO 59
<211> LENGTH: 729
<212> TYPE: DNA
<213> ORGANISM: Artificial
<220> FEATURE:
<223> OTHER INFORMATION: gene coding for scFv antibody fragment

<400> SEQUENCE: 59
gacgtggtgc tcactcagtc tccactcact ttgtcggtta ccattggaca accagcctcc     60
atctcttgca agtcaagtca gagcctctta gatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
ctcacgttcg gtgctgggac aaagttggaa attaaacggg gtggtggtgg atctggcggc    360
ggcggctctg gtggtggtgg atcccagctg cagctgcagc agtctggggc agagcttgtg    420
aggtcagggg cctcagtcaa gttgtcctgc acagcttctg gcttcaacat taagactac    480 tatatgaact gggtgaagca gaggcctgaa cagggcctgg agtggattgg atggattgat    540
cctgcgaatg gtgatactgc atatgccccg aggttccagg tcaaggccac tatgactgca    600
gacaaatcct ccaacacagc ctacctgcag ctcagcagcc tgacatctga ggacactgcc    660
gtctattact gtaatgctga tctccctatg gaccagtggg gtcaaggaac ctcagtcacc    720
gtctcctca                                                            729

<210> SEQ ID NO 60
<211> LENGTH: 63
<212> TYPE: DNA
<213> ORGANISM: Artificial
<220> FEATURE:
<223> OTHER INFORMATION: pET22B(+)

<400> SEQUENCE: 60
aaatacctgc tgccgaccgc tgctgctggt ctgctgctcc tcgctgccca gccggcgatg     60
gcc                                                                   63

<210> SEQ ID NO 61
<211> LENGTH: 255
<212> TYPE: PRT
<213> ORGANISM: Artificial
<220> FEATURE:
<223> OTHER INFORMATION: First mutant scFv antibody fragment

<400> SEQUENCE: 61

Asp Val Val Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

```
Pro Lys Arg Leu Ile Tyr Leu Val Ser Lys Leu Asp Ser Gly Val Pro
         50                  55                  60
Asp Arg Phe Thr Gly Ser Gly Ser Gly Thr Asp Phe Thr Leu Lys Ile
 65                  70                  75                  80
Ser Arg Val Glu Ala Glu Asp Leu Gly Val Tyr Tyr Cys Trp Gln Gly
                 85                  90                  95
Thr His Phe Pro Leu Thr Phe Gly Ala Gly Thr Lys Leu Glu Ile Lys
                100                 105                 110
Arg Gly Gly Gly Gly Ser Gly Gly Gly Ser Gly Gly Gly Gly Ser
            115                 120                 125
Gln Leu Gln Leu Gln Ser Gly Ala Glu Leu Val Arg Ser Gly Ala
    130                 135                 140
Ser Val Lys Leu Ser Cys Thr Ala Ser Gly Phe Asn Ile Lys Asp Tyr
145                 150                 155                 160
Tyr Met Asn Trp Val Lys Gln Arg Pro Glu Gln Gly Leu Glu Trp Ile
                165                 170                 175
Gly Trp Ile Asp Pro Ala Asn Gly Asp Thr Ala Tyr Ala Pro Arg Phe
            180                 185                 190
Gln Val Lys Ala Asp Met Thr Ala Asp Lys Asp Ser Asp Thr Ala Tyr
        195                 200                 205
Leu Gln Leu Ser Ser Leu Thr Ser Glu Asp Thr Ala Val Tyr Tyr Cys
    210                 215                 220
Asn Ala Asp Leu Pro Met Asp Gln Trp Gly Gln Gly Thr Ser Val Thr
225                 230                 235                 240
Val Ser Ser Ala Ala Ala Leu Glu Ser Phe Asn Arg Asn Glu Cys
                245                 250                 255

<210> SEQ ID NO 62
<211> LENGTH: 26
<212> TYPE: DNA
<213> ORGANISM: Artificial
<220> FEATURE:
<223> OTHER INFORMATION: Primer

<400> SEQUENCE: 62
gatattgtaa tgacccagtc tccatc                                   26

<210> SEQ ID NO 63
<211> LENGTH: 45
<212> TYPE: DNA
<213> ORGANISM: Artificial
<220> FEATURE:
<223> OTHER INFORMATION: Primer

<400> SEQUENCE: 63
catatgtaaa tctccttatt aaagttaaac aaaattattc tagag              45

<210> SEQ ID NO 64
<211> LENGTH: 30
<212> TYPE: DNA
<213> ORGANISM: Artificial
<220> FEATURE:
<223> OTHER INFORMATION: Primer

<400> SEQUENCE: 64
ggttaaagct ctcgagtgcg gccgctgagg                               30

<210> SEQ ID NO 65
<211> LENGTH: 30
<212> TYPE: DNA
```

<210> SEQ ID NO 65
<211> LENGTH: 30
<212> TYPE: DNA
<213> ORGANISM: Artificial
<220> FEATURE:
<223> OTHER INFORMATION: Primer

<400> SEQUENCE: 65
gcaacgaatg ctgagatccg gctgctaaca                               30

<210> SEQ ID NO 66
<211> LENGTH: 784
<212> TYPE: DNA
<213> ORGANISM: Artificial
<220> FEATURE:
<223> OTHER INFORMATION: base sequence coding for mutant scFv

<400> SEQUENCE: 66
gacgtggtgc tcactcagtc tccactcact ttgtcggtta ccattggaca accagcctcc    60
atctcttgca agtcaagtca gagcctctta gatagtgatg gaaagacata tttgaattgg   120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttcct   300
ctcacgttcg gtgctgggac aaagttggaa attaaacggg gtggtggtgg atctggcggc   360
ggcggctctg gtggtggtgg atcccagctg cagctgcagc agtctggggc agagcttgtg   420
aggtcagggg cctcagtcaa gttgtcctgc acagcttctg gcttcaacat taagactac   480 tatatgaact gggtgaagca gaggcctgaa cagggcctgg agtggattgg atggattgat   540
cctgcgaatg tgatactgc atatgccccg aggttccagg tcaaggccga tatgactgca   600
gacaaagatt ccgatacagc ctacctgcag ctcagcagcc tgacatctga ggacactgcc   660
gtctattact gtaatgctga tctccctatg gaccagtggg gtcaaggaac ctcagtcacc   720
gtctcctcag cggccgcact cgagagcttt aaccgcaacg aatgctgaga tccggctgct   780
aaca                                                               784

<210> SEQ ID NO 67
<211> LENGTH: 17
<212> TYPE: PRT
<213> ORGANISM: Artificial
<220> FEATURE:
<223> OTHER INFORMATION: Epitope of troponin I derived from human
      myocardium

<400> SEQUENCE: 67

Cys Gln Pro Leu Glu Leu Ala Gly Leu Gly Phe Ala Glu Leu Gln Asp
1               5                   10                  15

Leu

<210> SEQ ID NO 68
<211> LENGTH: 360
<212> TYPE: DNA
<213> ORGANISM: Artificial
<220> FEATURE:
<223> OTHER INFORMATION: DNA fragment coding for VH chain of
      monoclonal antibody

<400> SEQUENCE: 68
gaagtgaaac ttgaggagtc tggggggaggc ttagtgaagc ctggagggac cctgaaactc    60
tcctgtgcag cctctggatt cactttcagt agctatgcca tgtcttgggt tcgccagact   120
ccggagaaga ggctggactg ggtcgcaacc ataagtagtg gtggtagtta catcttctat   180

```
ccagacagtg tgaagggtcg attcaccatc tccagagaca atgccaggaa caccctgtac    240
ctgcaaatga acagtctgag gtctgaggat acggccatgt attactgtgc aagacaccat    300
aacccagaca gtcgggcttt gcttactggg gccaaggga ctctggtcac tgtctctgca    360
```

<210> SEQ ID NO 69
<211> LENGTH: 342
<212> TYPE: DNA
<213> ORGANISM: Artificial
<220> FEATURE:
<223> OTHER INFORMATION: DNA fragment coding for VL chain of monoclonal
      antibody

<400> SEQUENCE: 69

```
gatattgtaa tgacccagtc tccatcctcc ctggctatgt cagtaggaca gaaggtcact     60
atgagctgca agtccagtca gagccttttta aatagtagca tcaaaagaa ctatttggcc    120 tggtaccagc agaaaccagg acagtctcct aaacttctgg tatactttgc atccactagg    180
gaatctgggg tccctgatcg cttcataggc agtggatctg gacagattt cactcttacc    240 atcagcagtg tgcaggctga agacctggca gattacttct gtcagcaaca ttatagcact    300
cctctcacgt tcggtgctgg gaccaagctg gagctgaaac gg                       342
```

<210> SEQ ID NO 70
<211> LENGTH: 747
<212> TYPE: DNA
<213> ORGANISM: Artificial
<220> FEATURE:
<223> OTHER INFORMATION: DNA coding for scFv fragment

<400> SEQUENCE: 70

```
gatattgtaa tgacccagtc tccatcctcc ctggctatgt cagtaggaca gaaggtcact     60
atgagctgca agtccagtca gagccttttta aatagtagca tcaaaagaa ctatttggcc    120 tggtaccagc agaaaccagg acagtctcct aaacttctgg tatactttgc atccactagg    180
gaatctgggg tccctgatcg cttcataggc agtggatctg gacagattt cactcttacc    240 atcagcagtg tgcaggctga agacctggca gattacttct gtcagcaaca ttatagcact    300
cctctcacgt tcggtgctgg gaccaagctg gagctgaaac ggggtggtgg tggatctggc    360
ggcggcggct ctggtggtgg tggatccgaa gtgaaacttg aggagtctgg ggaggcttta    420
gtgaagcctg gagggaccct gaaactctcc tgtgcagcct ctggattcac tttcagtagc    480
tatgccatgt cttgggttcg ccagactccg gagaagaggc tggactgggt cgcaaccata    540
agtagtggtg gtagttacat cttctatcca gacagtgtga aggtcgatt caccatctcc    600 agagacaatg ccaggaacac cctgtacctg caaatgaaca gtctgaggtc tgaggatacg    660
gccatgtatt actgtgcaag acaccataac ccagacaagt cgggctttgc ttactggggc    720
caagggactc tggtcactgt ctctgca                                         747
```

<210> SEQ ID NO 71
<211> LENGTH: 261
<212> TYPE: PRT
<213> ORGANISM: Artificial
<220> FEATURE:
<223> OTHER INFORMATION: Second mutant scFv antibody fragment

<400> SEQUENCE: 71

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
```

```
            20                  25                  30
Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
50                  55                  60

Pro Lys Arg Phe Lys Gly Lys Gly Lys Thr Lys Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Arg Gly Gly Gly Gly Ser Gly Gly Gly Ser Gly Gly Gly
        115                 120                 125

Ser Glu Val Lys Leu Glu Ser Gly Gly Gly Leu Val Lys Pro Gly
    130                 135                 140

Gly Thr Leu Lys Leu Ser Cys Ala Ala Ser Gly Phe Thr Phe Ser Ser
145                 150                 155                 160

Tyr Ala Met Ser Trp Val Arg Gln Thr Pro Glu Lys Arg Leu Asp Trp
                165                 170                 175

Val Ala Thr Ile Ser Ser Gly Gly Ser Tyr Ile Phe Tyr Pro Asp Ser
            180                 185                 190

Val Lys Gly Arg Phe Thr Ile Ser Arg Asp Asn Ala Arg Asn Thr Leu
        195                 200                 205

Tyr Leu Gln Met Asn Ser Leu Arg Ser Glu Asp Thr Ala Met Tyr Tyr
    210                 215                 220

Cys Ala Arg His His Asn Pro Asp Lys Ser Gly Phe Ala Tyr Trp Gly
225                 230                 235                 240

Gln Gly Thr Leu Val Thr Val Ser Ala Ala Ala Leu Glu Ser Phe
                245                 250                 255

Asn Arg Asn Glu Cys
            260

<210> SEQ ID NO 72
<211> LENGTH: 30
<212> TYPE: DNA
<213> ORGANISM: Artificial
<220> FEATURE:
<223> OTHER INFORMATION: Primer

<400> SEQUENCE: 72
ggttaaagct ctcgagtgcg gccgcaagct                                    30

<210> SEQ ID NO 73
<211> LENGTH: 30
<212> TYPE: DNA
<213> ORGANISM: Artificial
<220> FEATURE:
<223> OTHER INFORMATION: Primer

<400> SEQUENCE: 73
gcaacgaatg ctgagatccg gctgctaaca                                    30

<210> SEQ ID NO 74
<211> LENGTH: 802
<212> TYPE: DNA
<213> ORGANISM: Artificial
<220> FEATURE:
<223> OTHER INFORMATION: base sequence coding for mutant scFv
```

```
<400> SEQUENCE: 74
gatattgtaa tgacccagtc tccatcctcc ctggctatgt cagtaggaca gaaggtcact      60
atgagctgca agtccagtca gagccttta  aatagtagca atcaaaagaa ctatttggcc     120
tggtaccagc agaaaccagg acagtctcct aaacttctgg tatactttgc atccactagg    180
gaatctgggg tccctaaacg cttcaaaggc aaaggaaaag ggacaaaatt cactcttacc    240
atcagcagtg tgcaggctga agacctggca gattacttct gtcagcaaca ttatagcact    300
cctctcacgt tcggtgctgg gaccaagctg gagctgaaac ggggtggtgg tggatctggc    360
ggcggcggct ctggtggtgg tggatccgaa gtgaaacttg aggagtctgg gggaggctta    420
gtgaagcctg agggacccct gaaactctcc tgtgcagcct ctggattcac tttcagtagc    480
tatgccatgt cttgggttcg ccagactccg gagaagaggc tggactgggt cgcaaccata    540
agtagtggtg gtagttacat cttctatcca gacagtgtga agggtcgatt caccatctcc    600
agagacaatg ccaggaacac cctgtacctg caaatgaaca gtctgaggtc tgaggatacg    660
gccatgtatt actgtgcaag acaccataac ccagacaagt cgggctttgc ttactggggc    720
caagggactc tggtcactgt ctctgcagcg gccgcactcg agagctttaa ccgcaacgaa    780
tgctgagatc cggctgctaa ca                                              802

<210> SEQ ID NO 75
<211> LENGTH: 28
<212> TYPE: PRT
<213> ORGANISM: Artificial
<220> FEATURE:
<223> OTHER INFORMATION: Linker

<400> SEQUENCE: 75

Cys Gly Gly Lys Gly Gly Lys Gly Gly Lys Gly Gly Lys Gly Gly Lys
1               5                   10                  15

Gly Gly Lys Gly Gly Lys Gly Gly Lys Gly Gly Cys
            20                  25

<210> SEQ ID NO 76
<211> LENGTH: 113
<212> TYPE: PRT
<213> ORGANISM: Artificial
<220> FEATURE:
<223> OTHER INFORMATION: VL of first mutant scFv antibody fragment

<400> SEQUENCE: 76

Asp Val Val Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Ile Lys
                100                 105                 110

Arg
```

-continued

```
<210> SEQ ID NO 77
<211> LENGTH: 127
<212> TYPE: PRT
<213> ORGANISM: Artificial
<220> FEATURE:
<223> OTHER INFORMATION: VH of first mutant scFv antibody fragment

<400> SEQUENCE: 77
```

Gln Leu Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met Asn Trp Val Lys Gln Arg Pro Glu Gln Gly Leu Glu Trp Ile
        35                  40                  45

Gly Trp Ile Asp Pro Ala Asn Gly Asp Thr Ala Tyr Ala Pro Arg Phe
    50                  55                  60

Gln Val Lys Ala Asp Met Thr Ala Asp Lys Ser Asp Thr Ala Tyr
65                  70                  75                  80

Leu Gln Leu Ser Ser Leu Thr Ser Glu Asp Thr Ala Val Tyr Tyr Cys
                85                  90                  95

Asn Ala Asp Leu Pro Met Asp Gln Trp Gly Gly Gly Thr Ser Val Thr
            100                 105                 110

Val Ser Ser Ala Ala Ala Leu Glu Ser Phe Asn Arg Asn Glu Cys
        115                 120                 125

```
<210> SEQ ID NO 78
<211> LENGTH: 114
<212> TYPE: PRT
<213> ORGANISM: Artificial
<220> FEATURE:
<223> OTHER INFORMATION: VL of second mutant scFv antibody fragment

<400> SEQUENCE: 78
```

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Lys Arg Phe Lys Gly Lys Gly Lys Gly Thr Lys Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Arg

```
<210> SEQ ID NO 79
<211> LENGTH: 132
<212> TYPE: PRT
<213> ORGANISM: Artificial
<220> FEATURE:
<223> OTHER INFORMATION: VH of second mutant scFv antibody fragment

<400> SEQUENCE: 79
```

Glu Val Lys Leu Glu Glu Ser Gly Gly Gly Leu Val Lys Pro Gly Gly
1               5                   10                  15

```
Thr Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Asp Trp Val
            35                  40                  45

Ala Thr Ile Ser Ser Gly Gly Ser Tyr Ile Phe Tyr Pro Asp Ser Val
        50                  55                  60

Lys Gly Arg Phe Thr Ile Ser Arg Asp Asn Ala Arg Asn Thr Leu Tyr
65                      70                  75                  80

Leu Gln Met Asn Ser Leu Arg Ser Glu Asp Thr Ala Met Tyr Tyr Cys
                    85                  90                  95

Ala Arg His His Asn Pro Asp Lys Ser Gly Phe Ala Tyr Trp Gly Gln
                100                 105                 110

Gly Thr Leu Val Thr Val Ser Ala Ala Ala Leu Glu Ser Phe Asn
            115                 120                 125

Arg Asn Glu Cys
        130

<210> SEQ ID NO 80
<211> LENGTH: 15
<212> TYPE: PRT
<213> ORGANISM: Artificial
<220> FEATURE:
<223> OTHER INFORMATION: Linker of first mutant scFv antibody fragment

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 15
<212> TYPE: PRT
<213> ORGANISM: Artificial
<220> FEATURE:
<223> OTHER INFORMATION: Linker of second mutant scFv antibody fragment

<400> SEQUENCE: 81

Gly Gly Gly Gly Ser Gly Gly Gly Gly Ser Gly Gly Gly Gly Ser
1               5                   10                  15
```

MUTANT PROTEIN CAPABLE OF BINDING SPECIFICALLY AND QUICKLY TO TROPONIN I DERIVED FROM HUMAN MYOCARDIUM

CROSS-REFERENCE TO RELATED APPLICATIONS

This is a continuation application of International Application No. PCT/JP2013/001067, with an international filing date of Feb. 25, 2013, which claims priority of Japanese Patent Application No. 2012-118180 filed on May 24, 2012, the entire content of which is incorporated herein by reference.

SEQUENCE LISTING

The application contains a Sequence Listing which has been submitted in ASCII format via EFS-Web and is hereby incorporated by reference in its entirety. Said ASCII copy, created on Apr. 4, 2014, is named SequenceListing_043887-0281.txt and is 28,841 bytes in size.

BACKGROUND

Technical Field

The technical field relates to a mutant protein capable of binding specifically and quickly to troponin I derived from human myocardium.

Non Patent Literature 1 and Non Patent Literature 2 disclose that a concentration of troponin I derived from myocardial increases rapidly in blood of a patient infected with acute myocardial infarction.

CITATION LIST

Non Patent Literature 1
Aleksei G. Katrukha et. al., "Troponin I is released in bloodstream of patients with acute myocardial infarction not in free form but as complex", Clinical Chemistry, Vol. 43, Issue 8, p.p. 1379-1385 (1997)
Non Patent Literature 2
Till Keller et. al., "Sensitive Troponin I Assay in Early Diagnosis of Acute Myocardinal Infarction", The NEW ENGLAND JOURNAL of MEDICINE, Vol. 361, pages 868-877 (2009)

SUMMARY

One non-limiting and exemplary embodiment provides a mutant protein capable of binding specifically and quickly to troponin I derived from human myocardium.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A mutant protein capable of binding specifically to troponin I derived from human myocardium, the mutant protein comprising:
a first mutant scFv antibody fragment 51;
a second mutant scFv antibody fragment 52; and
a linker 53, wherein the first mutant scFv antibody fragment 51 comprises a first light chain variable region 51L consisting of an amino acid sequence represented by SEQ ID NO; 76 and a first heavy chain variable region 51H consisting of an amino acid sequence represented by SEQ ID NO: 77;
the second mutant scFv antibody fragment 52 comprises a second light chain variable region 52L consisting of an amino acid sequence represented by SEQ ID NO: 78 and a second heavy chain variable region 52H consisting of an amino acid sequence represented by SEQ ID NO: 79;
the linker 53 comprises cysteine molecules at the N-terminus and C-terminus thereof;
the linker 53 is provided between the C-terminus of the first heavy chain variable region 51H and the C-terminus of the second heavy chain variable region 52H;
the linker 53 is bound to the C-terminus of the first heavy chain variable region 51H through a disulfide bond; and
the linker 53 is bound to the C-terminus of the second heavy chain variable region 52H through a disulfide bond.

The present disclosure provides a mutant protein capable of binding specifically and quickly to troponin I derived from human myocardium.

DETAILED DESCRIPTION

Figure 1:
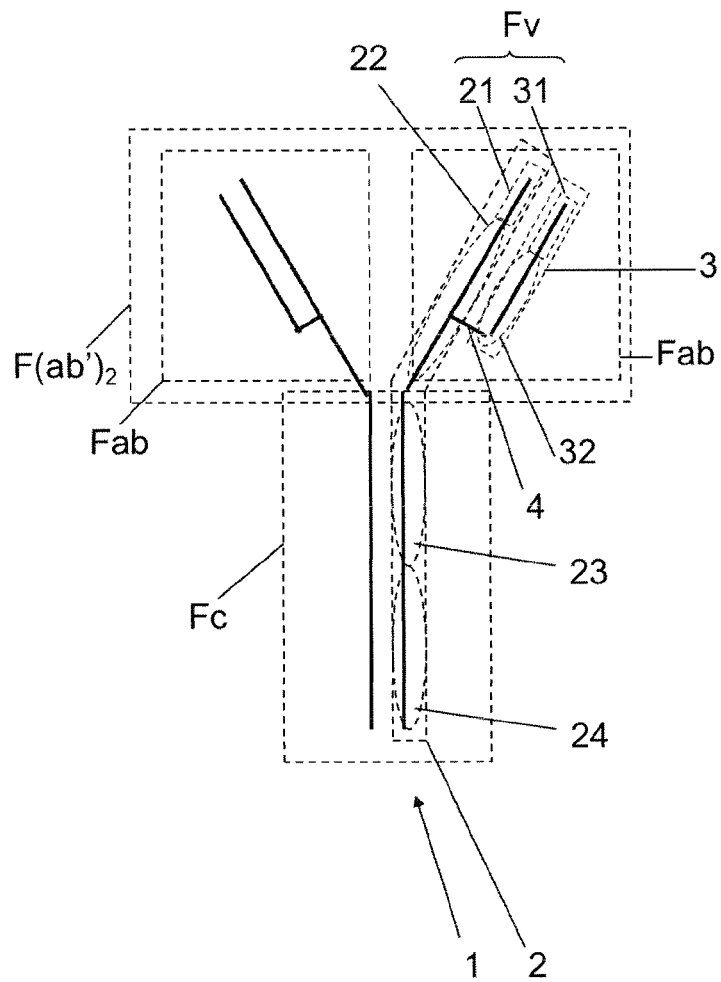
FIG. 1 shows an antibody. The antibody 1 consists of two Fab regions and one Fc region. It further consists of two heavy chains 2 and two light chains 3. Each heavy chain 2 consists of a heavy chain constant region 1 (referential sign: 22), a heavy chain constant region 2 (referential sign: 23), a heavy chain constant region 3 (referential sign: 24), and heavy chain variable region 21. Each light chain 3 consists of a light chain variable region 31 and a light chain constant region 32. Each Fab region consists of the one heavy chain variable region 21, the one heavy chain constant region 1 (referential sign: 22), the one light chain variable region 31, and the one light chain constant region 32. The light chain 3 is connected to the heavy chain 2 through a linker 4. The Fv region, consists of the heavy chain variable region 21 and the light chain variable region 31.

The embodiment of the present disclosure will be described below.
(Explanation of the Term)
First, the term used in the present specification is described.
FIG. 1 shows an antibody. As known well, the antibody 1 has a shape of the "Y" letter. The antibody 1 consists of two Fab regions and one Fc region. The antibody 1 consists of two heavy chains 2 and two light chains 3. Each heavy chain 2 consists of a heavy chain constant region 1 (referential sign: 22), a heavy chain constant region 2 (referential sign: 23), a heavy chain constant region 3 (referential sign: 24), and heavy chain variable region 21. Each light chain 3 consists of a light chain variable region 31 and a light chain constant region 32.

Each Fab region consists of the one heavy chain variable region 21, the one heavy chain constant region 1 (referential sign: 22), the one light chain variable region 31, and the one light chain constant region 32. The light chain 3 is connected to the heavy chain 2 through a linker 4. The heavy chain 2 has the heavy chain variable region 21 in the end thereof. The light chain 3 has the light chain variable region 31 in the end thereof. An antigen is specifically bound to the antibody 1. In more detail, the antigen is bound specifically to the Fv region, which consists of the heavy chain variable region 21 and the light chain variable region 31. In the present specification, the antigen is troponin I derived from human myocardium.

An example of the antibody fragment is an Fab antibody fragment, an $F(ab')_2$ antibody fragment, or an scFv antibody fragment.

The Fab antibody fragment consists of one Fab region. In other words, the Fab antibody fragment consists of the one light chain variable region 31, the one heavy chain variable region 21, the one light chain constant region 32, the one heavy chain constant region 1 (referential sign: 22), and the linker 4. The light chain constant region 32 is connected to the heavy chain constant region (referential sign: 22) through the linker 4.

The $F(ab')_2$ antibody fragments consists of two Fab regions. As above, each Fab region consists of the one light chain variable region 31, the one heavy chain variable region 21, the one light chain constant region 32, the one heavy chain constant region 1 (referential sign: 22), and the linker 4. These two Fab regions are connected to each other through another linker (not shown). For example, one heavy chain constant region 1 (referential sign: 22) is connected to the other heavy chain constant region 1 (referential sign: 22) through the another linker (not shown).

The scFv antibody fragment consists of the light chain variable region 31, the heavy chain variable region 21, and a linker. The light chain variable region 31 is connected to the heavy chain variable region 21 through the linker (not shown).

Figure 2:
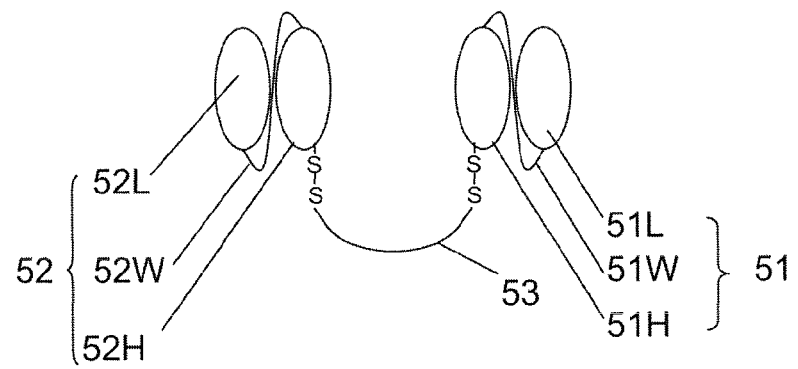
FIG. 2 schematically shows the mutant protein according to the present disclosure. The reference numbers in this figure are as follows: 51: First mutant scFv antibody fragment; 51L: First light chain variable region; 51H: First heavy chain variable region; 51W: First fragment linker; 52: Second mutant scFv antibody fragment; 52L: Second light chain variable region; 52H: Second heavy chain variable region; 52W: Second fragment linker; and 53: Linker (Intralinker).

As shown in FIG. 2, the mutant protein according to the present embodiment consists of a first mutant scFv antibody fragment 51, a second mutant scFv antibody fragment 52, and linker 53. The linker 53 is provided between the first mutant scFv antibody fragment 51 and the second mutant scFv antibody fragment 52. In order to distinguish from other linkers, this linker 53 may be referred to as "intralinker".

The first mutant scFv antibody fragment 51 comprises the first light chain variable region 51L consisting of the amino acid sequence represented by SEQ ID NO: 76 and the first heavy chain variable region 51H consisting of the amino acid sequence represented by SEQ ID NO: 77. A first fragment linker 51W is provided between the first light chain variable region 51L and the first heavy chain variable region 51H. An example of the first fragment linker 51W is GGGGSGGGGSGGGGS (SEQ ID NO: 80).

As one example, the first mutant scFv antibody fragment 51 consists of the amino acid sequence represented by SEQ ID NO: 61. In other words, the amino acid sequence represented by the SEQ ID NO: 61 is identical to the amino acid sequence obtained by connecting three amino acid sequences represented by SEQ ID NO: 76, SEQ ID NO: 80, and SEQ ID NO: 77 in this order.

The second mutant scFv antibody fragment 52 comprises the second light chain variable region 52L consisting of the amino acid sequence represented by SEQ ID NO: 78 and the second heavy chain variable region 52H consisting of the amino acid sequence represented by SEQ ID NO: 79. A second fragment linker 52W is provided between the first light chain variable region 52L and the second heavy chain variable region 52H. An example of the second fragment linker 52W is GGGGSGGGGSGGGGS (SEQ ID NO: 81).

As one example, the second mutant scFv antibody fragment 52 consists of the amino acid sequence represented by SEQ ID NO: 71. In other words, the amino acid sequence represented by the SEQ ID NO: 71 is identical to the amino acid sequence obtained by connecting three amino acid sequences represented by SEQ ID NO: 78, SEQ ID NO: 81, and SEQ ID NO: 79 in this order.

The intralinker 53 is provided between the first heavy chain variable region 51H consisting of the amino acid sequence represented by SEQ ID NO: 77 and the second heavy chain variable region 52H consisting of the amino acid sequence represented by SEQ ID NO: 79. More particularly, the intralinker 53 is interposed between the C-terminus of the first heavy chain variable region 51H and the C-terminus of the second heavy chain variable region 52H. As described in the SEQ ID NO: 77, the first heavy chain variable region 51H has a cysteine molecule in the C-terminus thereof. Similarly, as described in the SEQ ID NO: 79, the second heavy chain variable region 2H also has a cysteine molecule in the C-terminus thereof. Each of the N-terminus and C-terminus of the intralinker 53 also has a cysteine molecule.

Accordingly, the one cysteine molecule located at either the N-terminus or the C-terminus of the intralinker 53 reacts with the cysteine molecule located at the C-terminus of the first heavy chain variable region 51H consisting of the amino acid sequence represented by SEQ ID NO: 77 to form a disulfide bond. In this manner, the linker 53 binds to the C-terminus of the first heavy chain variable region 51H through the disulfide bond.

Similarly, the other cysteine molecule located at the C-terminus or N-terminus of the intralinker 53 reacts with the cysteine molecule located at the C-terminus of the second heavy chain variable region 52H consisting of the amino acid sequence represented by SEQ ID NO: 79 to form a disulfide bond. In this manner, the linker 53 binds to the C-terminus of the second heavy chain variable region 52H through the disulfide bond.

An example of the linker 53 is CGGKGGKGGKGGKGGKGGKGGKGGKGGC (SEQ ID NO: 75).

In this way, as shown in FIG. 2, the linker 53 is provided between the C-terminus of the first heavy chain variable region 51H and the C-terminus of the second heavy chain variable region 52H.

As long as the mutant protein according to the present embodiment is capable of binding to the troponin I derived from human myocardium specifically and quickly, the N-terminus of the first light chain variable region 51L may be modified with an amino acid sequence. The C-terminus may be also modified.

Similarly, as long as the mutant protein according to the present embodiment is capable of binding to the troponin I derived from human myocardium specifically and quickly, the N-terminus of the second light chain variable region 52L may be modified with an amino acid sequence. The C-terminus may be also modified.

As long as the mutant protein according to the present embodiment is capable of binding to the troponin I derived from human myocardium specifically and quickly, the N-terminus of the first heavy chain variable region 51H may be modified with an amino acid sequence.

Similarly, as long as the mutant protein according to the present embodiment is capable of binding to the troponin I derived from human myocardium specifically and quickly, the N-terminus of the second heavy chain variable region 52H may be modified with an amino acid sequence.

When the mutant protein according to the present embodiment is brought into contact with the troponin I derived from human myocardium, the mutant protein is bound to the troponin I derived from human myocardium specifically and quickly. More particularly, the mutant protein according to the present embodiment is mixed with the troponin I derived from human myocardium, the mutant protein is bound to the troponin I derived from human myocardium specifically and quickly.

The mutant protein according to the present embodiment may be produced with a conventional protein expression technique. More particularly, first, prepared is a vector comprising a gene sequence coding for the mutant protein according to the present embodiment. Next, a cell (e.g., *Escherichia coli*) is transfected with the vector. The cell is cultured to produce the mutant protein according to the present embodiment.

In order to obtain the scFv antibody fragment efficiently, it is desirable that the scFv antibody fragment is produced by a refolding method. Non Patent Literature 3 discloses the refolding method.

Non Patent Literature 3

Jun Kamishikiryo et. al., "Molecular Basis for LLT1 Protein Recognition by Human CD161 Protein (NKRP1A/KLRB1)", THE JOURNAL OF BIOLOGICAL CHEMISTRY, VOL. 286, NO. 27, p.p. 23823-23830.

Examples of the disclosed technique are as follows.

1st aspect: A mutant protein capable of binding specifically to troponin I derived from human myocardium, the mutant protein comprising:

a first mutant scFv antibody fragment 51;
a second mutant scFv antibody fragment 52; and
a linker 53, wherein the first mutant scFv antibody fragment 51 comprises a first light chain variable region 51L consisting of an amino acid sequence represented by SEQ ID NO: 76 and a first heavy chain variable region 51H consisting of an amino acid sequence represented by SEQ ID NO: 77;

the second mutant scFv antibody fragment 52 comprises a second light chain variable region 52L consisting of an amino acid sequence represented by SEQ ID NO: 78 and a second heavy chain variable region 52H consisting of an amino acid sequence represented by SEQ ID NO: 79;

the linker 53 comprises cysteine molecules at the N-terminus and C-terminus thereof;

the linker 53 is provided between the C-terminus of the first heavy chain variable region 51H and the C-terminus of the second heavy chain variable region 52H;

the linker 53 is bound to the C-terminus of the first heavy chain variable region 51H through a disulfide bond; and the linker 53 is bound to the C-terminus of the second heavy chain variable region 52H through a disulfide bond.

2nd aspect: A method for binding a mutant protein specifically to troponin I derived from human myocardium, the method comprising steps of:

(a) preparing the mutant protein; wherein
the mutant protein comprises:
a first mutant scFv antibody fragment 51;
a second mutant scFv antibody fragment 52; and
a linker 53, wherein
the first mutant scFv antibody fragment 51 comprises a first light chain variable region 51L consisting of an amino acid sequence represented by SEQ ID: 76 and a first heavy chain variable region 51H consisting of an amino acid sequence represented by SEQ ID: 77;

the second mutant scFv antibody fragment 52 comprises a second light chain variable region 52L consisting of an amino acid sequence represented by SEQ ID: 78 and a second heavy chain variable region 52H consisting of an amino acid sequence represented by SEQ ID: 79;

the linker 53 comprises cysteine molecules at the N-terminus and C-terminus thereof;

the linker 53 is provided between the C-terminus of the first heavy chain variable region 51H and the C-terminus of the second heavy chain variable region 52H;

the linker 53 is bound to the C-terminus of the first heavy chain variable region 51H through a disulfide bond; and the linker 53 is bound to the C-terminus of the second heavy chain variable region 52H through a disulfide bond; and (b) bringing the troponin I derived from human myocardium into contact with the mutant protein so as to bind the mutant protein specifically to the troponin I derived from human myocardium.

EXAMPLES

An example for supporting the present embodiment is described below.

Example 1

Table 1, Table 2, Table 3, and Table 4 show the primers used in the example 1.

Table 1 shows the forward mixture primers (primers 1-21, SEQ ID NOs: 02-22) for amplifying a light chain variable region.

Table 2 shows the forward mixture primers (primers 22-44, SEQ ID NOs: 23-45) for amplifying a heavy chain variable region.

Table 3 shows the reverse mixture primers (primers 45-49, SEQ ID NOs: 46-50) for amplifying a light chain variable region.

Table 4 shows the reverse mixture primers (primers 50-55, SEQ ID NOs: 51-56) for amplifying a heavy chain variable region.

TABLE 1

| Primer 1 | SEQ ID NO: 02 | CCTTTCTATGCGGCCCAGCCGGCCATGGCCGAY ATTGTWCTCWCCCARTC |
|---|---|---|
| Primer 2 | SEQ ID NO: 03 | CCTTTCTATGCGGCCCAGCCGGCCATGGCCGAY ATTSTGMTSACYCAGTC |
| Primer 3 | SEQ ID NO: 04 | CCTTTCTATGCGGCCCAGCCGGCCATGGCCGAY ATTGTGMTMACTCAGTC |
| Primer 4 | SEQ ID NO: 05 | CCTTTCTATGCGGCCCAGCCGGCCATGGCCGAY ATTGTGHTRWCACAGTC |
| Primer 5 | SEQ ID NO: 06 | CCTTTCTATGCGGCCCAGCCGGCCATGGCCGAY ATTGTRATGACMCAGTC |
| Primer 6 | SEQ ID NO: 07 | CCTTTCTATGCGGCCCAGCCGGCCATGGCCGAY ATTMAGATRAMCCAGTC |
| Primer 7 | SEQ ID NO: 08 | CCTTTCTATGCGGCCCAGCCGGCCATGGCCGAY ATTCAGATGAYDCAGTC |
| Primer 8 | SEQ ID NO: 09 | CCTTTCTATGCGGCCCAGCCGGCCATGGCCGAY ATTTTGCTGACTCAGTC |

TABLE 1-continued

| Primer | SEQ ID NO: | |
|---|---|---|
| Primer 9 | SEQ ID NO: 10 | CCTTTCTATGCGGCCCAGCCGGCCATGGCCGAYATTGTTCTCAWCCAGTC |
| Primer 10 | SEQ ID NO: 11 | CCTTTCTATGCGGCCCAGCCGGCCATGGCCGAYATTGWGCTSACCCAATC |
| Primer 11 | SEQ ID NO: 12 | CCTTTCTATGCGGCCCAGCCGGCCATGGCCGAYATTSTRATGACCCARTC |
| Primer 12 | SEQ ID NO: 13 | CCTTTCTATGCGGCCCAGCCGGCCATGGCCGAYRTTKTGATGACCCAVAC |
| Primer 13 | SEQ ID NO: 14 | CCTTTCTATGCGGCCCAGCCGGCCATGGCCGAYATYCAGATGACACAGAC |
| Primer 14 | SEQ ID NO: 15 | CCTTTCTATGCGGCCCAGCCGGCCATGGCCGAYATTGTGATGACACAACC |
| Primer 15 | SEQ ID NO: 16 | CCTTTCTATGCGGCCCAGCCGGCCATGGCCGAYATCCAGCTGACTCAGCC |
| Primer 16 | SEQ ID NO: 17 | CCTTTCTATGCGGCCCAGCCGGCCATGGCCGAYATTGTGATGACBCAGKC |
| Primer 17 | SEQ ID NO: 18 | CCTTTCTATGCGGCCCAGCCGGCCATGGCCGAYATTGTGATAACYCAGGA |
| Primer 18 | SEQ ID NO: 19 | CCTTTCTATGCGGCCCAGCCGGCCATGGCCGAYATTGTGATGACCCAGWT |
| Primer 19 | SEQ ID NO: 20 | CCTTTCTATGCGGCCCAGCCGGCCATGGCCGAYGTGSTGMTSACYCAGTC |
| Primer 20 | SEQ ID NO: 21 | CCTTTCTATGCGGCCCAGCCGGCCATGGCCGAYGCTGTTGTACTCAGGAATC |
| Primer 21 | SEQ ID NO: 22 | CCTTTCTATGCGGCCCAGCCGGCCATGGCCGAYATTGTDHTVWCHCAGTC |

TABLE 2

| Primer | SEQ ID NO: | |
|---|---|---|
| Primer 22 | SEQ ID NO: 23 | AGCGGCGGCGGCGGCTCTGGTGGTGGTGGATCCGAKGTRMAGCTTCAGGAGYC |
| Primer 23 | SEQ ID NO: 24 | AGCGGCGGCGGCGGCTCTGGTGGTGGTGGATCCGAGGTNCAGCTBCAGCAGTC |
| Primer 24 | SEQ ID NO: 25 | AGCGGCGGCGGCGGCTCTGGTGGTGGTGGATCCCAGGTGCAGCTGAAGSASTC |
| Primer 25 | SEQ ID NO: 26 | AGCGGCGGCGGCGGCTCTGGTGGTGGTGGATCCCAGSTBCAGCTGCAGCAGTC |
| Primer 26 | SEQ ID NO: 27 | AGCGGCGGCGGCGGCTCTGGTGGTGGTGGATCCGAGGTYCAGCTYCAGCAGTC |
| Primer 27 | SEQ ID NO: 28 | AGCGGCGGCGGCGGCTCTGGTGGTGGTGGATCCGARGTCCARCTGCAACARTC |
| Primer 28 | SEQ ID NO: 29 | AGCGGCGGCGGCGGCTCTGGTGGTGGTGGATCCCAGGTYCAGCTBCAGCARTC |
| Primer 29 | SEQ ID NO: 30 | AGCGGCGGCGGCGGCTCTGGTGGTGGTGGATCCCAGGTYCARCTKCAGCAGTC |
| Primer 30 | SEQ ID NO: 31 | AGCGGCGGCGGCGGCTCTGGTGGTGGTGGATCCCAGGTCCACGTGAAGCAGTC |
| Primer 31 | SEQ ID NO: 32 | AGCGGCGGCGGCGGCTCTGGTGGTGGTGGATCCGAGGTGAASSTGGTGGARTC |
| Primer 32 | SEQ ID NO: 33 | AGCGGCGGCGGCGGCTCTGGTGGTGGTGGATCCGAVGTGAWGYTGGTGGAGTC |
| Primer 33 | SEQ ID NO: 34 | AGCGGCGGCGGCGGCTCTGGTGGTGGTGGATCCGAGGTGAAGGTCATCGAGTC |
| Primer 34 | SEQ ID NO: 35 | AGCGGCGGCGGCGGCTCTGGTGGTGGTGGATCCSAGGTGCAGSKGGTGGAGTC |
| Primer 35 | SEQ ID NO: 36 | AGCGGCGGCGGCGGCTCTGGTGGTGGTGGATCCGAKGTGCAMCTGGTGGAGTC |
| Primer 36 | SEQ ID NO: 37 | AGCGGCGGCGGCGGCTCTGGTGGTGGTGGATCCGAAGTGCAVCTGGTGGAGTC |
| Primer 37 | SEQ ID NO: 38 | AGCGGCGGCGGCGGCTCTGGTGGTGGTGGATCCGAGGTGAAGCTGATGGARTC |
| Primer 38 | SEQ ID NO: 39 | AGCGGCGGCGGCGGCTCTGGTGGTGGTGGATCCGAGGTGCARCTTGTTGAGTC |
| Primer 39 | SEQ ID NO: 40 | AGCGGCGGCGGCGGCTCTGGTGGTGGTGGATCCGARGTRAAGCTTCTCGAGTC |
| Primer 40 | SEQ ID NO: 41 | AGCGGCGGCGGCGGCTCTGGTGGTGGTGGATCCGAAGTGAARSTTGAGGAGTC |
| Primer 41 | SEQ ID NO: 42 | AGCGGCGGCGGCGGCTCTGGTGGTGGTGGATCCGAAGTGATGCTGGTGGAGTC |
| Primer 42 | SEQ ID NO: 43 | AGCGGCGGCGGCGGCTCTGGTGGTGGTGGATCCCAGGTTACTCTRAAAGWGTSTG |
| Primer 43 | SEQ ID NO: 44 | AGCGGCGGCGGCGGCTCTGGTGGTGGTGGATCCCAGGTCCAAYTVCAGCARCC |
| Primer 44 | SEQ ID NO: 45 | AGCGGCGGCGGCGGCTCTGGTGGTGGTGGATCCGATGTGAACTTGGAAGTGTC |

TABLE 3

| Primer | SEQ ID NO: | |
|---|---|---|
| Primer 45 | SEQ ID NO: 46 | ACCAGAGCCGCCGCCGCCGCTACCACCACCACCCCGTTTGATTTCCARCTTKG |
| Primer 46 | SEQ ID NO: 47 | ACCAGAGCCGCCGCCGCCGCTACCACCACCACCCCGTTTTATTTCCAGCTTGG |
| Primer 47 | SEQ ID NO: 48 | ACCAGAGCCGCCGCCGCCGCTACCACCACCACCCCGTTTSAGCTCCAGCTTGG |
| Primer 48 | SEQ ID NO: 49 | ACCAGAGCCGCCGCCGCCGCTACCACCACCACCCCGTTYWATTTCCAACTTWG |
| Primer 49 | SEQ ID NO: 50 | ACCAGAGCCGCCGCCGCCGCTACCACCACCACCCCCTAGGACAGTCAGTTTGG |

TABLE 4

| Primer | SEQ ID NO: | |
|---|---|---|
| Primer 50 | SEQ ID NO: 51 | CGGCACCGGCGCACCTGCGGCCGCYGAGGAAACGGTGACCGTGGT |
| Primer 51 | SEQ ID NO: 52 | CGGCACCGGCGCACCTGCGGCCGCYGAGGAGACTGTGAGAGTGGT |
| Primer 52 | SEQ ID NO: 53 | CGGCACCGGCGCACCTGCGGCCGCYGAGGAGACGGTGACTGAGRT |
| Primer 53 | SEQ ID NO: 54 | CGGCACCGGCGCACCTGCGGCCGCYGAGGAAGACTGTAGAGTGGT |
| Primer 54 | SEQ ID NO: 55 | CGGCACCGGCGCACCTGCGGCCGCYGCGGAGACASTGACCAGAGT |
| Primer 55 | SEQ ID NO: 56 | CGGCACCGGCGCACCTGCGGCCGCYGCAGAGACASTGACCAGAGT |

(Preparation of the First Mutant scFv Antibody Fragment)

The first mutant scFv antibody fragment 51 consisting of the amino acid sequence represent by SEQ ID NO: 61 was prepared through the following step (a1), step (a2), step (b-1), step (b-2), step (b-3-1), step (b-3-2), step (b-4), step (c-1), step (c-2), and step (c-3).

Step (a1) Preparation of a Hybridoma (Derived from Mouse Spleen) Capable of Producing Monoclonal Antibodies which Specifically Binds to Troponin I Derived from Human Myocardium The amino acid (SEQ ID NO: 01, purchased from Sigma Aldrich Japan Co., Ltd., CRPAPAPIRRRSS-NYRAYATEPHAKKKSKISASRKLQLKTLLLQIAK) contained in troponin I derived from human myocardium was connected to human serum albumin (purchased from Sigma Aldrich Japan Co. Ltd.) using a sulfo-SMCC cross linker (purchased from Thermo Fischer Scientific Co., Ltd.).

More particularly, the sulfo-SMCC cross linker (0.5 mg) was dissolved in a phosphate buffered saline of 100 microliter so as to obtain a first aqueous solution. This first aqueous solution was left under a temperature of 50 degrees Celsius for ten minutes.

The human serum albumin (10 mg) was dissolved in one milliliter of a phosphate buffered saline to obtain a second aqueous solution.

The first aqueous solution was mixed with the second aqueous solution to obtain the mixture. The mixture was left at rest for 30 minutes. In this way, the sulfo-SMCC cross linker was connected to the human serum albumin.

The mixture was passed through a column (purchased from GE health care, trade name: PD10) to remove the unreacted sulfo-SMCC cross linker.

The above-mentioned amino acid (SEQ ID NO: 01, 1.5 mg) was dissolved in dimethylsulfoxide (hereinafter, referred to as "DMSO") to obtain a DMSO solution. The DMSO solution (100 microliters) was added to the mixture (1 mL) having a concentration of 2 mg/ml. Afterwards, the mixture is left overnight to connect the sulfo-SMCC cross linker to the amino acid (SEQ ID NO: 01).

In this way, human serum albumin modified with the amino acid sequence (SEQ ID NO: 01) contained in the troponin I was obtained. Hereinafter, this human serum albumin is referred to as "troponin-modified HSA".

A complete Freud adjuvant (purchased from Wako Pure Chemical Industries Co., Ltd.) and troponin-modified HSA were mixed to obtain a mixture. This mixture was injected to a BALB/c mouse. The BALB/c mouse is a kind of the albino mouse.

Two weeks later, a mixture of phosphate buffered saline (hereinafter, referred to as "PBS") and troponin-modified HSA was injected to the BALB/c mouse. This was repeated once again. In this way, the BALB/c mouse was immunized by troponin-modified HSA for one month. In other words, by feeding the mixture to the BALB/c mouse, antibodies for troponin-modified HSA were produced in the body of the BALB/c mouse.

The Spleen of the immunized BALB/c mouse was taken out. In accordance with the cell fusion method disclosed in Non Patent Literature 4, hybridomas were obtained. Afterwards, the hybridoma was incubated in a culture fluid. The number of hybridomas (cells) after the incubation was approximately $5 \times 10^6$. The hybridomas obtained in this way were capable of producing the monoclonal antibody which specifically bound to troponin I derived from human myocardium.

Non Patent Literature 4
G. Kohler et al., Nature, 256, 495(1975)

Step (a2) Extract of Total Mouse RNAs from the Hybridoma Cells

In order to destroy the cell membrane of the cultured hybridomas, one milliliter of TRIzol (Purchased from Invitrogen Co., Ltd.) was added to the culture fluid containing the hybridomas, and the culture fluid was stirred well.

Then, a chloroform liquid having a volume of 0.2 mL (degree of purity: 99.9%) was added to the culture fluid, and the culture fluid was stirred well again.

The culture fluid was subjected to a centrifugal separation at an acceleration of gravity of 117600 m/s$^2$ under a temperature of 4 degrees Celsius for 15 minutes. The supernatant (500 μL) was acquired. Isopropanol (500 μL) was added to the obtained supernatant and left at rest under room temperature for ten minutes.

The culture fluid was subject to a centrifugal separation having a condition identical to the above-mentioned condition. A seventy-five percent ethanol aqueous solution (1 mL) was added to the obtained precipitate so as to obtain an ethanol solution.

The ethanol solution was subjected to a centrifugal separation at an acceleration of gravity of 73500 m/s$^2$ for five minutes. The precipitate was dried. In this way, total mouse RNAs were obtained.

Step (b-1) Extract of mRNA from the Total Mouse mRNAs

Using an OligotexTM-dT30 <Super> mRNA Purification kit (purchased from Takara bio Co., Ltd.), an mRNA was extracted from the total mouse RNAs obtained in the step (a2).

RNase-free water (100 μL) was injected into a microtube. This microtube was set at a block incubater (purchased from ASTEC CO. LTD.) and heated under a temperature of 70 degrees Celsius for one hour.

The total mouse RNAs were dissolved in the RNase-free water (100 μL).

A 2× binding buffered solution (100 μL) included in the kit and an oligotex (10 μL) included in the kit were mixed with the RNase-free water (100 μL). Subsequently, the mixture was left at rest under a temperature of 70 degrees Celsius for three minutes. Furthermore, the mixture was left at rest under a room temperature for ten minutes.

The mixture was subjected to a centrifugal separation at an acceleration of gravity of 147000 m/s$^2$ for five minutes. The supernatant was removed, and the precipitate was suspended in Wash buffer (350 μL) included in the kit. The suspension liquid was supplied to a column included in the kit. The column was subjected to a centrifugal separation at an acceleration of gravity of 147000 m/s$^2$ for 30 seconds.

The Wash buffer (350 μL) was supplied to the column to wash the column. The column was subjected to a centrifugal separation at an acceleration of gravity of 147000 m/s$^2$ again for 30 seconds.

A microtube for sample collection was attached to the bottom of the column.

In order to extract mRNA contained in the column, RNase-free water (20 μL) contained in the microtube was supplied to the column. Subsequently, the column was subjected to a centrifugal separation at an acceleration of gravity of 147000 m/s$^2$ for three minutes. Again, RNase-free water (20 μL) was supplied to the column, and the column was subjected to a centrifugal separation at an acceleration of gravity of 147000 m/s$^2$ for three minutes.

Thus, the extract liquid containing the mRNA was obtained in the microtube.

(Step b-2) Reverse-Transcription from mRNA to cDNA

The mRNA contained in the obtained extract liquid was reverse-transcripted with reverse-transcriptase (purchased from Takara bio Co., Ltd, trade name: Primescript) to obtain a solution contain cDNA.

Step (b-3-1) Amplification of the Gene Coding for the Light Chain Variable Region Using the cDNA The gene fragment (SEQ ID NO: 58, hereinafter, referred to as "VL gene fragment") coding for the light chain variable region of the above-mentioned monoclonal antibody was amplified by a PCR method using the cDNA contained in the solution, the forward primers 1-21 (SEQ ID NOs: 02-22), and the reverse primers 45-49 (SEQ ID NOs: 46-50). The polymerase used in this PCR method was purchased from Takara bio Co., Ltd as a trade name of TaKaRa Ex Taq Hot start Version.

The protocol of this PCR method is shown in Table 5.

TABLE 5

| One cycle | ninety six degrees Celsius for thirty seconds<br>fifty two degrees Celsius for one minute<br>sixty eight degrees Celsius for one minute |
|---|---|

The number of the cycle: 35 times.

Finally, the solution was left at 68 degrees Celsius for four minutes. In this way, a PCR solution was obtained. This PCR solution contained the amplified VL gene segment (SEQ ID NO: 58).

For the confirmation and purification of the amplified VL gene fragment, the obtained PCR solution was subjected to an electrophoresis using a gel containing agarose having a concentration of 2% by weight.

Step (b-3-2) Amplification of the Gene Coding for the Heavy Chain Variable Region Using the cDNA The gene fragment (SEQ ID NO: 57, hereinafter, referred to as "VH gene fragment") coding for the heavy chain variable region of the above-mentioned monoclonal antibody was amplified by a PCR method using the cDNA contained in the solution, the forward primers 22-44 (SEQ ID NOs: 23-45), and the reverse primers 50-55 (SEQ ID NOs: 51-56). The polymerase used in this PCR method was purchased from Takara bio Co., Ltd as a trade name of TaKaRa Ex Taq Hot start Version.

The protocol of this PCR method was identical to that of the VL gene fragment.

Finally, the solution was left at 68 degrees Celsius for four minutes. In this way, a PCR solution was obtained. This PCR solution contained the amplified VH gene segment (SEQ ID NO: 57).

For the confirmation of the generation of the VH gene fragment and for the purification of the VH gene fragment, the obtained PCR solution was subjected to an electrophoresis using a gel containing agarose having a concentration of 2% by weight.

Step (b-4) Connection of the VL Gene Fragment and the VH Gene Fragment

The purified VH gene fragment (SEQ ID NO: 57) was connected to the purified VL gene fragment (SEQ ID NO: 58) using an overlap extension PCR method. In this way, the gene fragment (SEQ ID NO: 59, hereinafter, referred to as "scFv gene fragment") coding for the scFv antibody fragment of the above-mentioned monoclonal antibody was obtained. The obtained gene fragment (SEQ ID NO: 59) were modified with restriction enzyme sites Nco1 and Not1 at the 5'-end and 3'-end thereof, respectively.

Step (c-1) Introduction of the Gene to a Vector

The scFv gene fragment was ligated into a protein expression vector (purchased from Takara bio Co., Ltd, trade name: pET22b(+)). The detail of the ligation is described below.

First, the scFv gene fragment was treated with restriction enzymes Nco1 and Not1 (both of which were purchased from Takara bio Co., Ltd.). The scFv gene fragment was purified by an electrophoresis method to obtain an aqueous solution containing the scFv gene fragment.

The protein expression vector was also treated with restriction enzymes Nco1 and Not1 (both of which were purchased from Takara bio Co., Ltd.). The protein expression vector was purified by an electrophoresis method to obtain an aqueous solution containing the protein expression vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into the protein expression vector.

Escherichia coli (purchased from Takara bio Co., Ltd., trade name; DH5α competent cell) was transfected with the protein expression vector in which the scFv gene fragment was thus ligated.

Subsequently, the Escherichia coli was incubated for sixteen hours on a LB plate culture medium containing ampicillin having a concentration of 100 μg/mL. After the incubation, single colony formed on the LB plate culture medium was picked up. The single colony was supplied to a LB liquid culture medium (5 mL) containing ampicillin having a concentration of 100 μg/mL, and the colony was incubated for 16 hours.

In order to remove an unnecessary gene sequence included in the protein expression vector pET22b(+), the protein expression vector pET22b(+) was extracted from this LB liquid culture medium using a kit (QIAGEN Co., Ltd. trade name: QIAprep spin miniprep kit). By a PCR method using the extracted protein expression vector pET22b(+), the primer 56 (SEQ ID NO: 67), and the primer 57 (SEQ ID NO: 68), the signal sequence (DNA sequence, SEQ ID NO: 60) of the protein expression vector pET22b(+) was removed. Thus, the expression vector coding for the wild type scFv antibody fragment was obtained.

Step (c-2) Substitution of the Sequence to the Vector

The expression vector obtained in the step (c-1) includes the scFv gene fragment (SEQ ID NO: 59). Among the sequence included in this expression vector, the base sequence CACCACCACCACCACCAC was substituted with AGCTTTAACCGCAACGAATGC.

More particularly, as shown in FIG. 2, a PCR method using the primer 58 (SEQ ID NO: 64), the primer 59 (SEQ ID NO: 65), and the expression vector obtained in the step (c-1) was performed. The primer 58 (SEQ ID NO: 64) was complementary to a part of the gene sequence of the vector including the scFv gene fragment, except for the ten bases to be substituted. The primer 59 (SEQ ID NO: 65) was complementary to a part of the gene sequence of the vector including the scFv gene fragment except for the eleven bases to be substituted. The PCR method shown in FIG. 3 allowed the eighteen bases included in the expression vector coding for the wild type scFv antibody fragment to be substituted with the another twenty-one bases. Thus, the expression vector containing the gene sequence (SEQ ID NO: 66) coding for the mutant scFv antibody fragment was obtained.

Step (c-3) Acquisition of the Protein Using the Vector

Escherichia coli (purchased from Takara bio Co., Ltd, trade name: BL21(DE3)) was transfected with the vector obtained in the step (c-2). Subsequently, this Escherichia coli was incubated on a LB plate culture medium containing ampicillin having a concentration of 100 μg/mL under a temperature of 37 degrees Celsius for 16 hours.

After the incubation, a single colony formed on the LB plate culture medium was picked up. The single colony was supplied to an LB liquid culture medium containing ampicillin (500 mL) having a concentration of 100 μg/mL. Subsequently, the *Escherichia coli* contained in the single colony was propagated in such a manner that the absorbance of the LB liquid culture medium at a wavelength of 600 nanometers was adjusted to 0.5.

Furthermore, an aqueous solution of isopropyl beta-D-thiogalactopyranoside (0.5 mL) having a concentration of 1M was added to the LB liquid culture medium. Afterwards, the *Escherichia coli* was incubated while it was incubated on shaking under a temperature of 37 degrees Celsius for five hours. In this way, a culture fluid was obtained.

The obtained culture fluid was subjected to a centrifugal separation at an acceleration of gravity of 49000 m/s$^2$ under a temperature of 4 degrees Celsius for five minutes. The precipitation containing the *Escherichia coli* was again suspended in a phosphate buffered saline (50 mL).

The suspension was subjected to an ultrasonic treatment to crush the *Escherichia coli*. The solution containing the crushed *Escherichia coli* was subjected to a centrifugal separation at an acceleration of gravity of 98000 m/s$^2$ under a temperature bottom of 4 degrees Celsius for thirty minutes. In this way, the precipitation was obtained.

The precipitation was washed twice with a phosphate buffered saline containing a surface active agent (purchased from Wako Pure Chemical Industries Co., Ltd., trade name: TritonX-100) having a concentration of 4%. The precipitation was washed with a phosphate buffered saline not containing a surface active agent.

An aqueous solution A (10 mL) containing chemical reagents shown in Table 6 was added to the precipitation.

TABLE 6

| Chemical reagents | Concentration |
|---|---|
| Guanidine hydrochloride | 6M |
| Sodium chloride | 0.1M |
| MES buffer solution | 50 mM |
| Ethylene diamine tetraacetic acid | 10 mM |

The aqueous solution A had a pH of 6.

Subsequently, the aqueous solution A was left under a temperature of 4 degrees Celsius for eighteen hours. In this way, the precipitation was dissolved.

The aqueous solution A was passed through a filter (purchased from Sartorius, trade name: Minisart) having a mesh size of 0.45 μm to remove the residue. In this way, the filtrate was obtained.

The aqueous solution B (2 mL) containing chemical reagents shown in Table 7 were added dropwise to the filtrate (1 mL).

TABLE 7

| Chemical reagents | Concentration |
|---|---|
| Tris-HCl | 0.1M |
| Ethylene diamine tetraacetic acid | 2 mM |
| Arginine hydrochloride | 1.0M |
| Cystamine | 3.73 mM |
| Cysteamine hydrochloride | 6.73 mM |

The aqueous solution B had a pH of 8.0. In this way, the aqueous solution having a volume of 3 mL was obtained.

The aqueous solution (3 mL) was added dropwise to the aqueous solution B having a volume of one liter. Afterwards, the obtained aqueous solution was stirred under a temperature of 4 degrees Celsius for 96 hours. In this way, the first mutant scFv antibody fragment (reference sign: 51, SEQ ID NO: 61) was obtained.

Subsequently, the solution was condensed using a filtration unit (purchased from Sartorius, trade name: VIVAFLOW50) so that the solution had a volume of 10 milliliter. The first mutant scFv antibody fragment contained in the solution was purified with a column (purchased from GE healthcare, trade name: HiLoad 26/60 Superdex pg).

(Preparation of the Second Mutant scFv Antibody Fragment)

The second mutant scFv antibody fragment 52 consisting of the amino acid sequence represent by SEQ ID NO: 71 was prepared through the following step (d1), step (d2), step (e-1), step (e-2), step (e-3-1), step (e-3-2), step (e-4), step (f-1), step (f-2), and step (f-3).

Step (d1) Preparation of a Hybridoma (Derived from Mouse Spleen) Capable of Producing Monoclonal Antibodies which Specifically Binds to Troponin I Derived from Human Myocardium The amino acid (SEQ ID NO: 67, purchased from Sigma Aldrich Japan Co., Ltd., CQPLELAGLGFAELQDL) contained in troponin I derived from human myocardium was connected to human serum albumin (purchased from Sigma Aldrich Japan Co. Ltd.) using a sulfo-SMCC cross linker (purchased from Thermo Fischer Scientific Co., Ltd.).

More particularly, the sulfo-SMCC cross linker (0.5 mg) was dissolved in a phosphate buffered saline of 100 microliter so as to obtain a first aqueous solution. This first aqueous solution was left under a temperature of 50 degrees Celsius for ten minutes.

The human serum albumin (10 mg) was dissolved in one milliliter of a phosphate buffered saline to obtain a second aqueous solution.

The first aqueous solution was mixed with the second aqueous solution to obtain the mixture. The mixture was left at rest for 30 minutes. In this way, the sulfo-SMCC cross linker was connected to the human serum albumin.

The mixture was passed through a column (purchased from GE health care, trade name: PD10) to remove the unreacted sulfo-SMCC cross linker.

The above-mentioned amino acid (SEQ ID NO: 67, 1.5 mg) was dissolved in dimethylsulfoxide (hereinafter, referred to as "DMSO") to obtain a DMSO solution. The DMSO solution (100 microliters) was added to the mixture (1 mL) having a concentration of 2 mg/ml. Afterwards, the mixture is left overnight to connect the sulfo-SMCC cross linker to the amino acid (SEQ ID NO: 67).

In this way, human serum albumin modified with the amino acid sequence (SEQ ID NO: 67) contained in the troponin I was obtained. Hereinafter, this human serum albumin is referred to as "troponin-modified HSA".

A complete Freud adjuvant (purchased from Wako Pure Chemical Industries Co., Ltd.) and troponin-modified HSA were mixed to obtain a mixture. This mixture was injected to a BALB/c mouse. The BALB/c mouse is a kind of the albino mouse.

Two weeks later, a mixture of phosphate buffered saline (hereinafter, referred to as "PBS") and troponin-modified HSA was injected to the BALB/c mouse. This was repeated once again. In this way, the BALB/c mouse was immunized by troponin-modified HSA for one month. In other words, by feeding the mixture to the BALB/c mouse, antibodies for troponin-modified HSA were produced in the body of the BALB/c mouse.

The Spleen of the immunized BALB/c mouse was taken out. In accordance with the cell fusion method disclosed in Non Patent Literature 4, hybridomas were obtained. Afterwards, the hybridoma was incubated in a culture fluid. The number of hybridomas (cells) after the incubation was approximately $5 \times 10^6$. The hybridomas obtained in this way were capable of producing the monoclonal antibody which specifically bound to troponin I derived from human myocardium.

Step (d2) Extract of Total Mouse RNAs from the Hybridoma Cells

In order to destroy the cell membrane of the cultured hybridomas, one milliliter of TRIzol (Purchased from Invitrogen Co., Ltd.) was added to the culture fluid containing the hybridomas, and the culture fluid was stirred well.

Then, a chloroform liquid having a volume of 0.2 mL (degree of purity: 99.9%) was added to the culture fluid, and the culture fluid was stirred well again.

The culture fluid was subjected to a centrifugal separation at an acceleration of gravity of 117600 m/s$^2$ under a temperature of 4 degrees Celsius for 15 minutes. The supernatant (500 µL) was acquired. Isopropanol (500 µL) was added to the obtained supernatant and left at rest under room temperature for ten minutes.

The culture fluid was subject to a centrifugal separation having a condition identical to the above-mentioned condition. A seventy-five percent ethanol aqueous solution (1 mL) was added to the obtained precipitate so as to obtain an ethanol solution.

The ethanol solution was subjected to a centrifugal separation at an acceleration of gravity of 73500 m/s$^2$ for five minutes. The precipitate was dried. In this way, total mouse RNAs were obtained.

Step (e-1) Extract of mRNA from the Total Mouse mRNAs

Using an OligotexTM-dT30 <Super> mRNA Purification kit (purchased from Takara bio Co., Ltd.), an mRNA was extracted from the total mouse RNAs obtained in the step (a2).

RNase-free water (100 µL) was injected into a microtube. This microtube was set at a block incubater (purchased from ASTEC CO. LTD.) and heated under a temperature of 70 degrees Celsius for one hour.

The total mouse RNAs were dissolved in the RNase-free water (100 µL).

A 2× binding buffered solution (100 µL) included in the kit and an oligotex (10 µL) included in the kit were mixed with the RNase-free water (100 µL). Subsequently, the mixture was left at rest under a temperature of 70 degrees Celsius for three minutes. Furthermore, the mixture was left at rest under a room temperature for ten minutes.

The mixture was subjected to a centrifugal separation at an acceleration of gravity of 147000 m/s$^2$ for five minutes. The supernatant was removed, and the precipitate was suspended in Wash buffer (350 µL) included in the kit. The suspension liquid was supplied to a column included in the kit. The column was subjected to a centrifugal separation at an acceleration of gravity of 147000 m/s$^2$ for 30 seconds.

The Wash buffer (350 µL) was supplied to the column to wash the column. The column was subjected to a centrifugal separation at an acceleration of gravity of 147000 m/s$^2$ again for 30 seconds.

A microtube for sample collection was attached to the bottom of the column.

In order to extract mRNA contained in the column, RNase-free water (20 µL) contained in the microtube was supplied to the column. Subsequently, the column was subjected to a centrifugal separation at an acceleration of gravity of 147000 m/s$^2$ for three minutes. Again, RNase-free water (20 µL) was supplied to the column, and the column was subjected to a centrifugal separation at an acceleration of gravity of 147000 m/s$^2$ for three minutes.

Thus, the extract liquid containing the mRNA was obtained in the microtube.

(Step e-2) Reverse-Transcription from mRNA to cDNA

The mRNA contained in the obtained extract liquid was reverse-transcripted with reverse-transcriptase (purchased from Takara bio Co., Ltd, trade name: Primescript) to obtain a solution contain cDNA.

Step (e-3-1) Amplification of the Gene Coding for the Light Chain Variable Region Using the cDNA The gene fragment (SEQ ID NO: 58, hereinafter, referred to as "VL gene fragment") coding for the light chain variable region of the above-mentioned monoclonal antibody was amplified by a PCR method using the cDNA contained in the solution, the forward primers 1-21 (SEQ ID NOs: 02-22), and the reverse primers 45-49 (SEQ ID NOs: 46-50). The polymerase used in this PCR method was purchased from Takara bio Co., Ltd as a trade name of TaKaRa Ex Taq Hot start Version.

The protocol of this PCR method is shown in Table 8.

TABLE 8

| One cycle | ninety six degrees Celsius for thirty seconds |
| --- | --- |
| | fifty two degrees Celsius for one minute |
| | sixty eight degrees Celsius for one minute |

The number of the cycle: 35 times.

Finally, the solution was left at 68 degrees Celsius for four minutes. In this way, a PCR solution was obtained. This PCR solution contained the amplified VL gene segment (SEQ ID NO: 58).

For the confirmation and purification of the amplified VL gene fragment, the obtained PCR solution was subjected to an electrophoresis using a gel containing agarose having a concentration of 2% by weight.

Step (e-3-2) Amplification of the Gene Coding for the Heavy Chain Variable Region Using the cDNA The gene fragment (SEQ ID NO: 57, hereinafter, referred to as "VH gene fragment") coding for the heavy chain variable region of the above-mentioned monoclonal antibody was amplified by a PCR method using the cDNA contained in the solution, the forward primers 22-44 (SEQ ID NOs: 23-45), and the reverse primers 50-55 (SEQ ID NOs: 51-56). The polymerase used in this PCR method was purchased from Takara bio Co., Ltd as a trade name of TaKaRa Ex Taq Hot start Version.

The protocol of this PCR method was identical to that of the VL gene fragment.

Finally, the solution was left at 68 degrees Celsius for four minutes. In this way, a PCR solution was obtained. This PCR solution contained the amplified VH gene segment (SEQ ID NO: 57).

For the confirmation of the generation of the VH gene fragment and for the purification of the VH gene fragment, the obtained PCR solution was subjected to an electrophoresis using a gel containing agarose having a concentration of 2% by weight.

Step (e-4) Connection of the VL Gene Fragment and the VH Gene Fragment

The purified VH gene fragment (SEQ ID NO: 57) was connected to the purified VL gene fragment (SEQ ID NO: 58) using an overlap extension PCR method. In this way, the gene fragment (SEQ ID NO: 59, hereinafter, referred to as "scFv gene fragment") coding for the scFv antibody fragment of the above-mentioned monoclonal antibody was obtained. The obtained gene fragment (SEQ ID NO: 59) were modified with restriction enzyme sites Nco1 and Not1 at the 5'-end and 3'-end thereof, respectively.

Step (f-1) Introduction of the Gene to a Vector

The scFv gene fragment was ligated into a protein expression vector (purchased from Takara bio Co., Ltd, trade name: pET22b(+)). The detail of the ligation is described below.

First, the scFv gene fragment was treated with restriction enzymes Nco1 and Not1 (both of which were purchased from Takara bio Co., Ltd.). The scFv gene fragment was purified by an electrophoresis method to obtain an aqueous solution containing the scFv gene fragment.

The protein expression vector was also treated with restriction enzymes Nco1 and Not1 (both of which were purchased from Takara bio Co., Ltd.). The protein expression vector was purified by an electrophoresis method to obtain an aqueous solution containing the protein expression vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into the protein expression vector.

*Escherichia coli* (purchased from Takara bio Co., Ltd., trade name; DH5α competent cell) was transfected with the protein expression vector in which the scFv gene fragment was thus ligated.

Subsequently, the *Escherichia coli* was incubated for sixteen hours on a LB plate culture medium containing ampicillin having a concentration of 100 µg/mL. After the incubation, single colony formed on the LB plate culture medium was picked up. The single colony was supplied to a LB liquid culture medium (5 mL) containing ampicillin having a concentration of 100 µg/mL, and the colony was incubated for 16 hours.

In order to remove an unnecessary gene sequence included in the protein expression vector pET22b(+), the protein expression vector pET22b(+) was extracted from this LB liquid culture medium using a kit (QIAGEN Co., Ltd. trade name: QIAprep spin miniprep kit). By a PCR method using the extracted protein expression vector pET22b(+), the primer 56 (SEQ ID NO: 67), and the primer 57 (SEQ ID NO: 68), the signal sequence (DNA sequence, SEQ ID NO: 60) of the protein expression vector pET22b(+) was removed. Thus, the expression vector coding for the wild type scFv antibody fragment was obtained.

Step (f-2) Substitution of the Sequence to the Vector

The expression vector obtained in the step (c-1) includes the scFv gene fragment (SEQ ID NO: 59). Among the sequence included in this expression vector, the base sequence CACCACCACCACCACCAC was substituted with AGCTTTAACCGCAACGAATGC.

Figure 3:
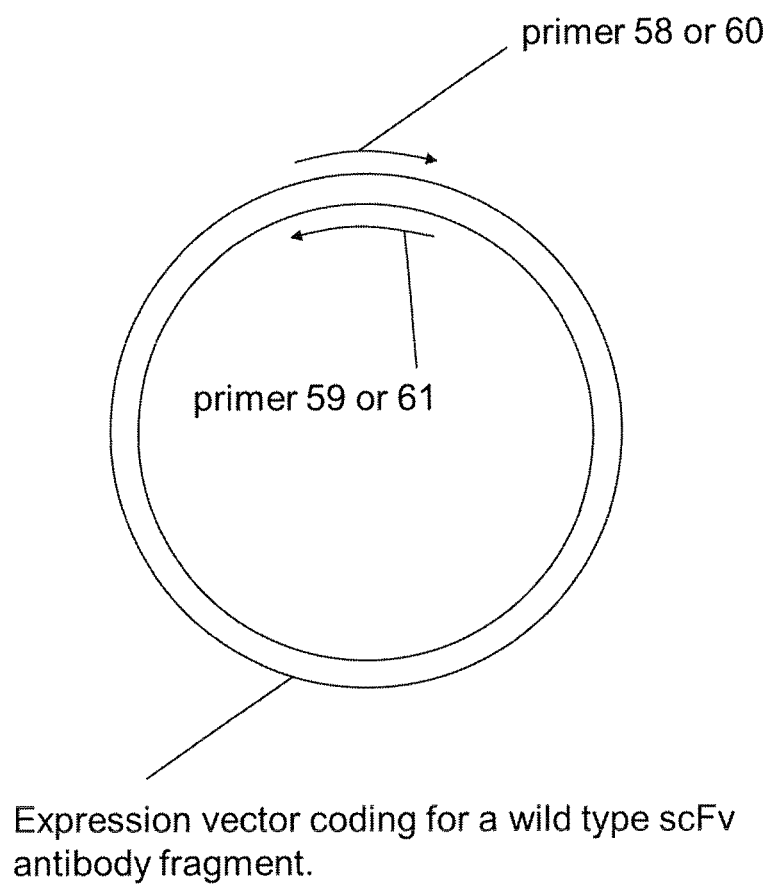
FIG. 3 shows the PCR method in the step (c-2) and the step (f-2) included in the example. The reference numbers in this figure are as follows: primer 58: SEQ ID NO:64; primer 59: SEQ ID NO: 65; primer 60: SEQ ID NO: 72; primer 61: SEQ ID NO: 73.

More particularly, as shown in FIG. 3, a PCR method using the primer 60 (SEQ ID NO: 72), the primer 61 (SEQ ID NO: 73), and the expression vector obtained in the step (c-1) was performed. The primer 60 (SEQ ID NO: 72) was complementary to a part of the gene sequence of the vector including the scFv gene fragment, except for the ten bases to be substituted. The primer 61 (SEQ ID NO: 73) was complementary to a part of the gene sequence of the vector including the scFv gene fragment except for the eleven bases to be substituted. The PCR method shown in FIG. 3 allowed the eighteen bases included in the expression vector coding for the wild type scFv antibody fragment to be substituted with the another twenty-one bases. Thus, the expression vector containing the gene sequence (SEQ ID NO: 74) coding for the mutant scFv antibody fragment was obtained.

Step (f-3) Acquisition of the Protein Using the Vector

*Escherichia coli* (purchased from Takara bio Co., Ltd, trade name: BL21(DE3)) was transfected with the vector obtained in the step (c-2). Subsequently, this *Escherichia coli* was incubated on a LB plate culture medium containing ampicillin having a concentration of 100 µg/mL under a temperature of 37 degrees Celsius for 16 hours.

After the incubation, a single colony formed on the LB plate culture medium was picked up. The single colony was supplied to an LB liquid culture medium containing ampicillin (500 mL) having a concentration of 100 µg/mL. Subsequently, the *Escherichia coli* contained in the single colony was propagated in such a manner that the absorbance of the LB liquid culture medium at a wavelength of 600 nanometers was adjusted to 0.5.

Furthermore, an aqueous solution of isopropyl beta-D-thiogalactopyranoside (0.5 mL) having a concentration of 1M was added to the LB liquid culture medium. Afterwards, the *Escherichia coli* was incubated while it was incubated on shaking under a temperature of 37 degrees Celsius for five hours. In this way, a culture fluid was obtained.

The obtained culture fluid was subjected to a centrifugal separation at an acceleration of gravity of 49000 m/s$^2$ under a temperature of 4 degrees Celsius for five minutes. The precipitation containing the *Escherichia coli* was again suspended in a phosphate buffered saline (50 mL).

The suspension was subjected to an ultrasonic treatment to crush the *Escherichia coli*. The solution containing the crushed *Escherichia coli* was subjected to a centrifugal separation at an acceleration of gravity of 98000 m/s$^2$ under a temperature bottom of 4 degrees Celsius for thirty minutes. In this way, the precipitation was obtained.

The precipitation was washed twice with a phosphate buffered saline containing a surface active agent (purchased from Wako Pure Chemical Industries Co., Ltd., trade name: TritonX-100) having a concentration of 4%. The precipitation was washed with a phosphate buffered saline not containing a surface active agent.

An aqueous solution A (10 mL) containing chemical reagents shown in Table 9 was added to the precipitation.

TABLE 9

| Chemical reagents | Concentration |
| --- | --- |
| Guanidine hydrochloride | 6M |
| Sodium chloride | 0.1M |
| MES buffer solution | 50 mM |
| Ethylene diamine tetraacetic acid | 10 mM |

The aqueous solution A had a pH of 6.

Subsequently, the aqueous solution A was left under a temperature of 4 degrees Celsius for eighteen hours. In this way, the precipitation was dissolved.

The aqueous solution A was passed through a filter (purchased from Sartorius, trade name: Minisart) having a mesh size of 0.45 µm to remove the residue. In this way, the filtrate was obtained.

The aqueous solution B (2 mL) containing chemical reagents shown in Table 10 were added dropwise to the filtrate (1 mL).

TABLE 10

| Chemical reagents | Concentration |
| --- | --- |
| Tris-HCl | 0.1M |
| Ethylene diamine tetraacetic acid | 2 mM |
| Arginine hydrochloride | 1.0M |
| Cystamine | 3.73 mM |
| Cysteamine hydrochloride | 6.73 mM |

The aqueous solution B had a pH of 8.0. In this way, the aqueous solution having a volume of 3 mL was obtained.

The aqueous solution (3 mL) was added dropwise to the aqueous solution B having a volume of one liter. Afterwards, the obtained aqueous solution was stirred under a temperature of 4 degrees Celsius for 96 hours. In this way, the second mutant scFv antibody fragment (reference sign: 52, SEQ ID NO: 71) was obtained.

Subsequently, the solution was condensed using a filtration unit (purchased from Sartorius, trade name: VIVAFLOW50) so that the solution had a volume of 10 milliliter. The second mutant scFv antibody fragment contained in the solution was purified with a column (purchased from GE healthcare, trade name: HiLoad 26/60 Superdex pg).

Step (g): Preparation of the Mutant Protein

The first mutant scFv antibody fragment (SEQ ID NO: 61), the second mutant scFv antibody fragment (SEQ ID NO: 71), and the peptide consisting of the amino acid sequence represented by SEQ ID NO: 75 were mixed at the molar ratio of 1:1:5 in a Tris hydrochloric acid buffer solution (50 mM, pH: 9.0) to obtain a mixture. The mixture was left at rest under a temperature of 4 degrees Celsius for 12 hours. In this way, as shown in FIG. 2, obtained was the mutant protein where the first mutant scFv antibody fragment (reference sign: 51, SEQ ID NO: 61), the intralinker 53 consisting of the amino acid sequence represented by SEQ ID NO: 75, and the second mutant scFv antibody fragment (reference sign: 52, SEQ ID 71) were connected in this order.

Subsequently, the mixture was purified with a chromatography column (Superdex75 5/150 GL, GE healthcare).

The Tris hydrochloric acid buffer solution (50 mM, pH: 9.0) was substituted with a Tris hydrochloric acid buffer solution (50 mM, pH: 7.4). Finally, the mutant protein was purified with a cation-exchange column (HiTrap SP HP, GE healthcare).

Measurement of the Association Rate

Using an intermolecular interaction analyzer Biacore T100 (purchased from GE health care company), the association rate of the mutant protein was measured in accordance with the manual attached to the intermolecular interaction analyzer Biacore T100.

More particularly, Troponin I (purchased from Funakoshi) derived from human myocardium having approximately 500 RU (Resonance Unit) was fixed on a CM5 chip (purchased from GE health care company). This CM5 chip was set in the Biacore T100. Then, aqueous solutions (concentration: 100 nM, 50 nM, 25 nM, 12.5 nM, and 6.25 nM, volume: 150 microliters) containing the purified mutant protein was flowed through the Biacore T100 to measure the association rate of the mutant protein. Table 11 shows the result.

Reference Example 1

The association rate of the mutant first scFv antibody fragment (SEQ ID NO: 61) was measured similarly to the above. Table 11 shows the result.

Reference Example 2

The association rate of the mutant second scFv antibody fragment (SEQ ID NO: 71) was measured similarly to the above. Table 11 shows the result.

TABLE 11

| | | Association Rate $K_a(M^{-1})$ |
| --- | --- | --- |
| Example | Mutant protein | 9.78E+11 |
| Reference example 1 | First mutant scFv antibody fragment | 5.11E+9 |
| Reference example 2 | Second mutant scFv antibody fragment | 3.85E+8 |

As is clear from Table 11, the mutant protein has much greater association rate Ka than the first and second mutant scFv antibody fragments. For this reason, the mutant protein is bound more strongly to the Troponin I derived from the human myocardium specifically, compared to the case where either the first or second mutant scFv antibody fragment is used.

INDUSTRIAL APPLICABILITY

The mutant protein according to the present disclosure can be used for a sensor for detecting acute myocardial infarction.

REFERENCE SIGNS LIST

51: First mutant scFv antibody fragment
51L: First light chain variable region
51H: First heavy chain variable region
51W: First fragment linker
52: Second mutant scFv antibody fragment
52L: Second light chain variable region
52H: Second heavy chain variable region
52W: Second fragment linker
53: Linker (Intralinker)

What is claimed is:

1. A mutant protein capable of binding specifically to troponin I derived from human myocardium, the mutant protein comprising:
   a first mutant scFv antibody fragment;
   a second mutant scFv antibody fragment; and a linker, wherein the first mutant scFv antibody fragment comprises a first light chain variable region consisting of an amino acid sequence represented by SEQ ID NO: 76 and a first heavy chain variable region consisting of an amino acid sequence represented by SEQ ID NO: 77;

the second mutant scFv antibody fragment comprises a second light chain variable region consisting of an amino acid sequence represented by SEQ ID NO: 78 and a second heavy chain variable region consisting of an amino acid sequence represented by SEQ ID NO: 79;

the linker comprises cysteine molecules at the N-terminus and C-terminus thereof;

the linker is provided between the C-terminus of the first heavy chain variable region and the C-terminus of the second heavy chain variable region;

the linker is bound to the C-terminus of the first heavy chain variable region through a disulfide bond; and the linker is bound to the C-terminus of the second heavy chain variable region through a disulfide bond.

2. A method for binding a mutant protein specifically to troponin I derived from human myocardium, the method comprising steps of:

(a) preparing the mutant protein; wherein the mutant protein comprises:

a first mutant scFv antibody fragment;

a second mutant scFv antibody fragment; and a linker, wherein the first mutant scFv antibody fragment comprises a first light chain variable region consisting of an amino acid sequence represented by SEQ ID NO: 76 and a first heavy chain variable region consisting of an amino acid sequence represented by SEQ ID NO: 77;

the second mutant scFv antibody fragment comprises a second light chain variable region consisting of an amino acid sequence represented by SEQ ID NO: 78 and a second heavy chain variable region consisting of an amino acid sequence represented by SEQ ID NO: 79;

the linker comprises cysteine molecules at the N-terminus and C-terminus thereof;

the linker is provided between the C-terminus of the first heavy chain variable region and the C-terminus of the second heavy chain variable region;

the linker is bound to the C terminus of the first heavy chain variable region through a disulfide bond; and the linker is bound to the C-terminus of the second heavy chain variable region through a disulfide bond; and (b) bringing the troponin I derived from human myocardium into contact with the mutant protein so as to bind the mutant protein to the troponin I derived from human myocardium specifically.

* * * * *